(12) United States Patent
Young et al.

(10) Patent No.: US 6,770,446 B1
(45) Date of Patent: Aug. 3, 2004

(54) CELL SYSTEMS HAVING SPECIFIC INTERACTION OF PEPTIDE BINDING PAIRS

(75) Inventors: Kathleen H. Young, Newtown, PA (US); Jian Cao, Monmouth Junction, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/556,390

(22) Filed: Apr. 24, 2000

Related U.S. Application Data

(63) Continuation-in-part of application No. 09/305,483, filed on May 6, 1999, now Pat. No. 6,284,519, which is a continuation of application No. 08/259,609, filed on Jun. 14, 1994, now Pat. No. 5,989,808.

(51) Int. Cl.$^7$ .......................... G01N 33/53; C12Q 1/66; C12N 1/14; C12N 1/16; C12N 1/18

(52) U.S. Cl. .......................... 435/7.1; 8/254.2; 8/254.21

(58) Field of Search .......................... 435/7.1, 8, 254.2, 435/254.21, 4, 6

(56) References Cited

U.S. PATENT DOCUMENTS

| | | | | |
|---|---|---|---|---|
| 5,283,173 A | * | 2/1994 | Fields et al. .................... | 435/6 |
| 5,512,473 A | | 4/1996 | Brent et al. ............. | 435/252.33 |
| 5,525,490 A | * | 6/1996 | Erickson et al. ............... | 435/29 |
| 5,580,979 A | * | 12/1996 | Bachovin | |
| 5,582,995 A | | 12/1996 | Avruch et al. ................ | 435/7.1 |
| 5,641,641 A | * | 6/1997 | Wood ............................ | 435/8 |
| 5,834,209 A | * | 11/1998 | Korsmeyer ................ | 435/7.1 |
| 5,837,478 A | * | 11/1998 | Gallatin et al. ............ | 435/7.24 |
| 5,989,808 A | * | 11/1999 | Young et al. .................. | 435/6 |
| 6,284,519 B1 | * | 9/2001 | Young et al. | |

FOREIGN PATENT DOCUMENTS

| | | |
|---|---|---|
| WO | WO 94/09133 | 4/1994 |
| WO | WO 95/18380 | 7/1995 |
| WO | WO 95/19988 | 7/1995 |
| WO | 95/26400 | 10/1995 |

OTHER PUBLICATIONS

Wu et al, Cell 74:1061–1070 (1993).*
Klein et al., J. Biomolecular Screening, 2 (1):41–49 (1997).*
Mendelsohn et al., Curr. Opin. Biotech. 5:482–486 (1994).*
Ozenberger et al., in The Yeast Two–Hybrid System, (P. Bartel and S. Fields, eds_ Oxford University Press, In., New York, pp. 158–172 (1997).*
Phyizicky et al., Microbiological Reviews, 59 (1):94–123 (1995).*
Catterall, Nature Biotechnology 16 (1): 906 (1998).*
Fields et al., Trends in Genetics, 10 (8):286–292 (1994).*
Fields et al., Nature 340:245–266 (1989).*
Kim et al., Nature, 362:841–844 (1993).*
Vojtek et al (1993) Cell 74:205–214.*

Abstract for Dual–Luciferase® Reporter 1000 Assay System Technical Manual, Abstract. (1999).
Aflalo, C., Targeting of Cloned Firefly Luciferase to Yeast Mitochondria, Biochemistry, vol. 29, pp. 4758–4766 (1990).
Boylan et al., Fused Bacterial Luciferase Subunits Catalyze Light Emission in Eukaryotes and Prokaryotes, The Journal of Biological Chemistry, vol. 264, No. 4, Issue of Feb. 5, pp. 1915–1918 (1989).
Chien et al., The Two Hybrid System: A Method to Identify and Clone Genes for Proteins That Interact With a Protein of Interest, Proceedings of the National Academy of Sciences of USA, 88:9578–82 (1991).
De Wet et al., Firefly Luciferase Gene: Structure and Expression in Mammalian Cells, Molecular and Cellular Biology, vol. 7, No. 2, pp. 725–737 (Feb. 1987).
Dohlman et al., Annu. Rev. Biochem., 60:653–88 (1991).
Dower S., Advances in Second Messenger and Phosphorprotein Research, 28:19–25 (1993).
Durfee et al., Genes and Devel., 7:555–69 (1993).
Fritz, C., et al., Current Biology, 2:403–05 (1992).
Garbers, The guanylyl cyclase receptor family, New Biol., vol. 2(6):499–504 (1990) (Abstract).
Himes et al., Assays for Transcriptional Activity Based on the Luciferase Reporter Gene, Methods in Molecular Biology, vol. 130, Transcription Factor Protocols, M.J. Timms (ed.), pp. 165–174, (2000).
Naylor, L. H., Reporter Gene Technology: The Future Looks Bright, Biochemical Pharmacology, vol. 58, pp. 749–757 (1999).
Silverman et al., New assay technologies for high–throughput screening, Current Opinion in Chemical Biology 2:397–403 (1998).

(List continued on next page.)

*Primary Examiner*—Terry McKelvey
*Assistant Examiner*—Nancy T. Vogel
(74) *Attorney, Agent, or Firm*—Finnegan, Henderson, Farabow, Garrett & Dunner, L.L.P.

(57) ABSTRACT

This invention relates to novel modified host cells which express heterologous fused proteins and methods of screening for test samples having peptide-binding activity; wherein the modified host cell comprises: (a) a gene sequence encoding a heterologous fusion protein; said fusion protein comprising a first peptide of a peptide binding pair, or segment of said first peptide, which is joined to either a DNA binding domain or its corresponding transcriptional activation domain of a transcriptional activation protein; (b) a gene sequence encoding a heterologous fusion protein, said fusion protein comprising a second peptide of the peptide binding pair in (a), or a segment thereof, fused to either a DNA binding domain or its corresponding transcriptional activation domain, whichever one is not employed in (a); (c) a luciferase gene operatively associated with the transcriptional activation protein, or a portion thereof; (d) optionally, a deletion or mutation in the chromosomal DNA of the host cell for the transcriptional activation protein if present in the selected host cell.

68 Claims, 12 Drawing Sheets

OTHER PUBLICATIONS

Stables et al., Development of a Dual Glow–Signal Firefly and Renilla Luciferase Assay Reagent for the Analysis of G–Protein Coupled Receptor Signaling, J. of Receptor & Signal Transduction Research, 19(1–4), 395–410 (1999).

Tatsumi et al., Synthesis of Enzymatically Active Firefly Luciferase in Yeast, Agric. Biol. Chem., 52(5), pp. 1123–1127 (1988).

Vieites et al., Expression and in vivo Determination of Firefly Luciferase as Gene Reporter in *Saccharomyes cerevisiae*, Yeast, vol. 10: 1321–1327 (1994).

Vojtek et al., Mammalian Ras Interacts Directly with the Serine/Threonine Kinase Raf, Cell, 74: 205–14 (1993).

Wang et al., Science, 265:674–76 (1994).

Yamaguchi et al., The primary structure of the rat guanylyl cyclase A/atrial natriuretic peptide receptor gene, J. Biol. Chem., vol. 265(33):20414–20 (1990) (Abstract).

Yang et al., A Protein Kinase Substrate Identified by the Two–Hybrid System Science; 257:680–82 (1992).

Young et al., Current Biology, 3:408–20 (1992).

Young, A yeast two–hybrid, systems based approach for the identification of novel pharmaceutical entities, Exp. Opin. Ther. Patents, vol. 9(7): 897–915 (1999).

\* cited by examiner

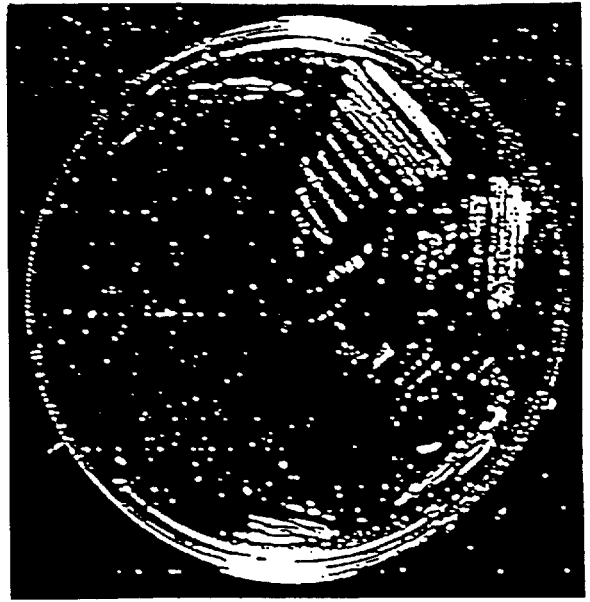
FIG. 2A
FIG. 2B

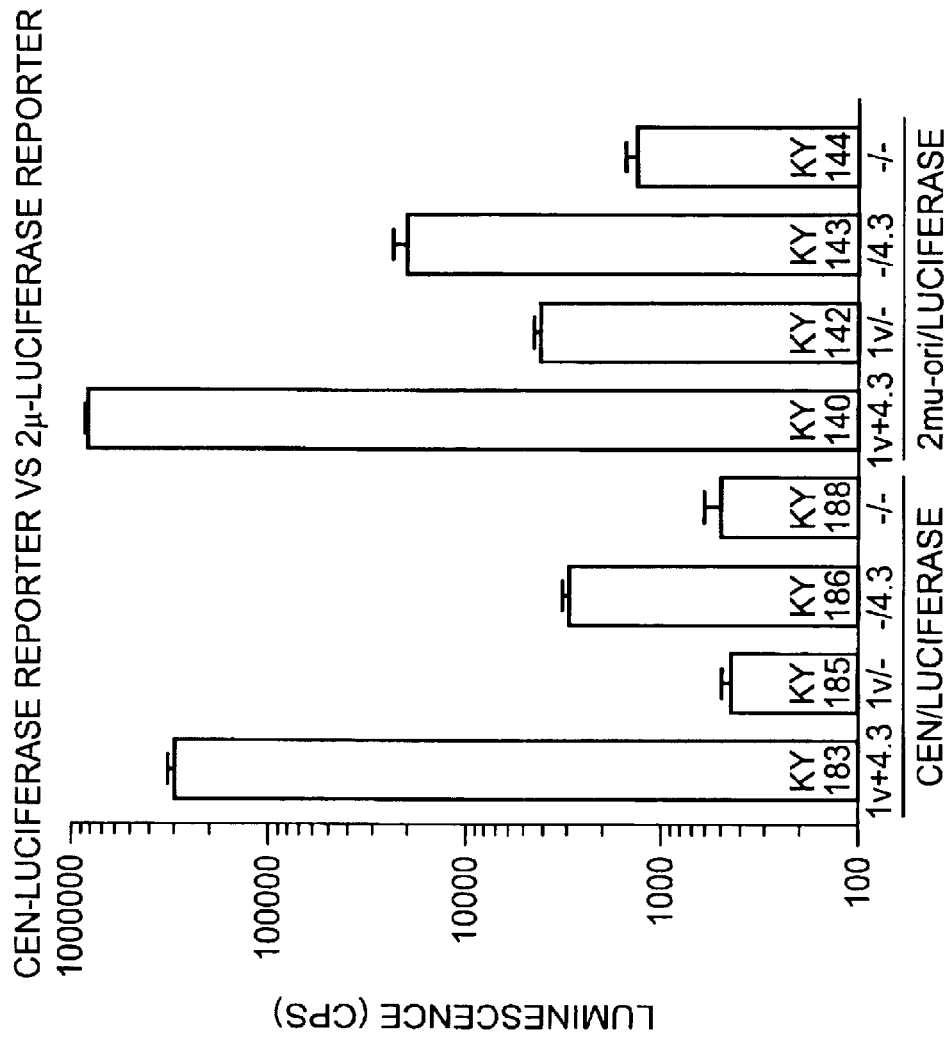

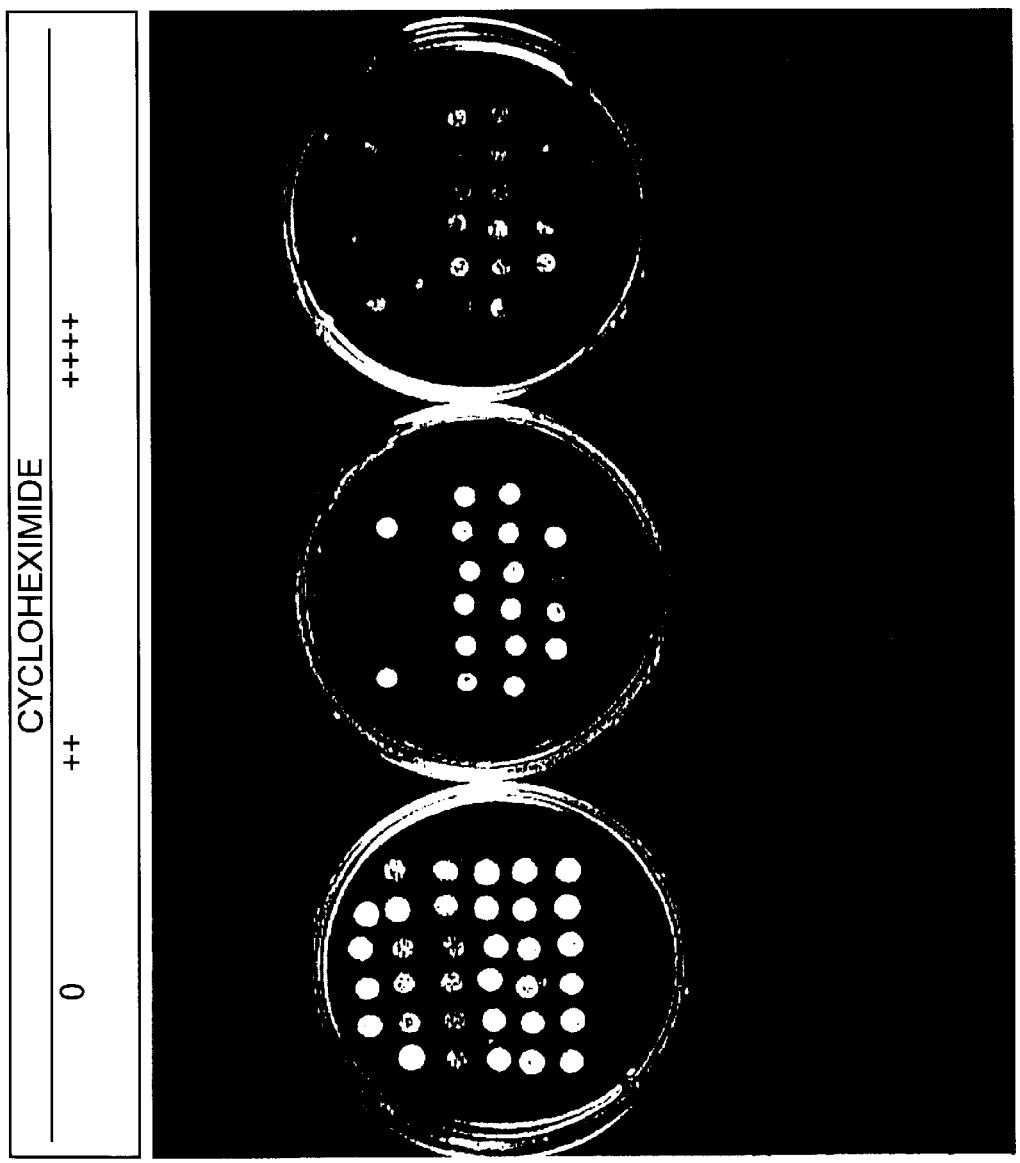

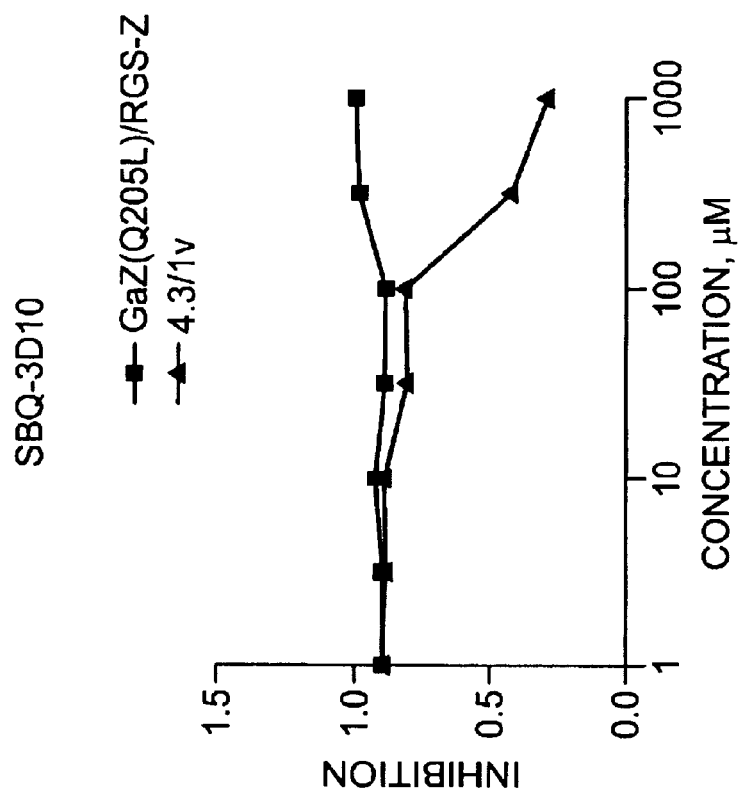
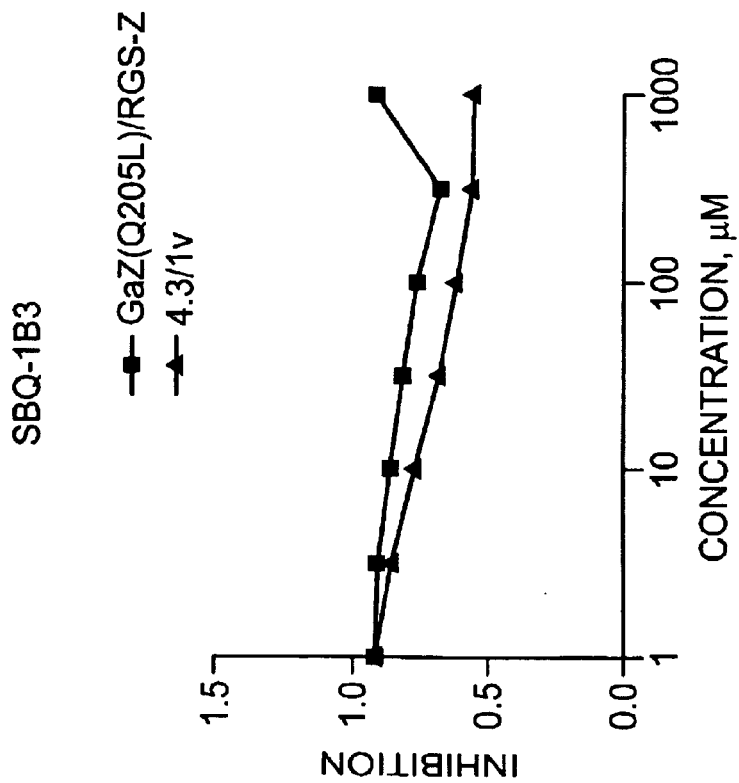

CELL SYSTEMS HAVING SPECIFIC INTERACTION OF PEPTIDE BINDING PAIRS

This application is a continuation-in-part of application Ser. No. 09/305,483, filed May 6, 1999, now U.S. Pat. No. 6,284,519, which is a continuation of application Ser. No. 08/259,609, filed Jun. 14, 1994, now U.S. Pat. No. 5,989,808, which are incorporated by reference herein.

FIELD OF THE INVENTION

This invention relates to novel cells which express heterologous fused proteins and methods of screening for compounds having peptide-binding activity, wherein the methods employ the novel cells of the invention.

BACKGROUND OF THE INVENTION

The specific binding of a pair of peptides to each other triggers a vast number of functions in a living cell. For example, the specific binding of a ligand to a surface receptor serves as the trigger for cellular responses to many external signals. In mammals, cells respond to a wide variety of circulating peptide hormones, often through single transmembrane domain receptors. It is certainly recognized that the cytokine receptor superfamily illustrates the diverse aspects of cellular function and physiological responses. Recent examinations of cytokine receptor function have revealed differing ligand-receptor protein stoichiometries including both 2-protein (ligand/receptor) (Cunningham et al., 1991; Staten et al., 1993). and 3-protein (ligand/receptor/receptor or ligand/receptor/transducer) interactions (Young, 1992; Taga and Kishimoto, 1992; Mui and Miyajima, 1994). The intricacies of such protein associations have been investigated using in vitro, often laborious, methods (Fuh et al., 1992; 1993; Davis et al., 1993) because easily manipulated genetic expression systems have been unavailable. The present invention is directed to novel, modified host systems that can be used for such investigations of protein-protein interactions. These novel systems are significantly less laborious than existing methods.

Recently reported systems in the art refer to a "2-hybrid" system as discussed by Fields and Song (1989) and also by Chein et al. (1991). The 2-hybrid system involves differential interactions between the separable DNA binding and activation domains of the yeast transcriptional activator Gal4. Heterologous proteins are expressed as hybrid proteins fused to either half of Gal4 (see FIG. 1; Fields and Song, 1989; Chein et al., 1991 for discussion of the 2-hybrid system). The positive interaction of the heterologous proteins brings the two halves of the Gal4 protein in close proximity, activating expression of a scorable reporter gene. Many yeast-based platforms link the desired effect of a gene or drug of interest to a change in yeast cell phenotype through the use of reporter genes. In yeast systems, reporter genes have commonly focused on auxotrophy genes for cell growth on selective media, or the LacZ gene for colorometric endpoint using assays that detect B-galactosidase activity. Here, we describe in-depth the applied utility of luciferase, for example, from *Renilla reniformis* or *Photinus pyralis,* as a reporter gene in yeast. Although luciferase has been used extensively as a reporter gene in mammalian cells, analogous use in yeast has not been reported. We have designed, validated and implemented luciferase reporter(s) for use in various yeast platforms, such as yeast two-hybrid for protein interaction studies. Yeast two-hybrid luciferase reporters provide increases in assay sensitivity, speed, ease, signal:noise ratios, and provide high quality quantitative data to yeast-based assays for a myriad of target identification and drug discovery applications. Use of the luciferase reporter gene in yeast provides substantial improvements to yeast-based assays as used for gene identification, protein-protein interaction identification and characterization, high throughput screening platforms, automation of these platforms, investigations of G-protein coupled receptors (GPCRs), regulation of GPCR signaling pathways, and ion channel studies.

Two-hybrid systems are useful for determining whether a first test peptide sequence has binding activity for a second known peptide sequence, wherein the affinity of the test peptide for the known peptide is unknown. Such a system has been used to analyze intracellular proteins such as transcription factors and kinase-target protein interactions (Yang et al., 1992; Durfee et al., 1993; Li et al., 1994).

The novel modified yeast cells of this invention, which use luciferase as a reporter gene, and the novel methods incorporating these cells provide a significant advance for the study and discovery of peptide mimics, including ligand mimics and receptor mimics. At this time, no one has developed an efficient and specific screening system to investigate these areas. By employing in a cell a peptide binding pair for which the binding affinity is known, the present invention permits the investigation of peptide binding pairs, such as a ligand and receptor, wherein the peptides bind via extracellular interactions. The present invention creates exponential advantages for the discovery of compounds which can interact as ligands for specific receptors or transducers. Potential ligands include, but are not limited to, mammalian hormones with the receptors being a cognate extracellular ligand-binding peptide. Furthermore, the present invention describes the use of cell systems which express multiple heterologous proteins, including the two heterologous fused proteins to establish the specific and reversible binding of the ligand and receptor. The specific interaction of the above-described binding is readily detected by a measurable change in cellular phenotype, for example, growth on selective medium.

SUMMARY OF THE INVENTION

One aspect of the present invention relates to the novel modified host cells for the expression of heterologous fusion proteins. The novel modified host cells comprise:

a) a gene sequence encoding a heterologous fusion protein; said fusion protein comprising a first peptide of a peptide binding pair, or segment of said first peptide, which is joined to either a DNA binding domain or its corresponding transcriptional activation domain of a transcriptional activation protein;

b) a gene sequence encoding a heterologous fusion protein, said fusion protein comprising a second peptide of the peptide binding pair in (a), or a segment of said second peptide, fused to either a DNA binding domain or its corresponding transcriptional activation domain, whichever one is not employed in (a);

c) a reporter gene operatively associated with the transcriptional activation protein, or a portion thereof.

d) optionally, a deletion or mutation in the chromosomal DNA of the yeast host cell for the transcriptional activation protein if present in the host cell.

The novel modified host cells of the present invention can be used to determine the interaction of a test sample with a selected peptide of a peptide binding pair. For example, the cell can be used to determine the interaction of a test sample with a selected ligand or receptor.

A second aspect of the present invention relates to novel modified cells and screening methods which indicate the interaction of a test sample with a selected peptide and receptor by a recognizable change in phenotype. The cell exhibits the change in phenotype only in the presence of a test compound having binding affinity for a peptide of the peptide binding pair, for example, binding affinity for a ligand or its receptor.

A third aspect of the present invention relates to novel cells and screening methods which permit determining to which peptide of a peptide binding pair a test sample binds.

A fourth aspect of the present invention relates to novel cells which express three or more heterologous components for the study of higher order multi-protein associations between three or more peptides, for example, such as the study of ligand dependent dimerization.

A fifth aspect of the present invention relates to novel yeast cells comprising a luciferase gene as a reporter gene and screening methods that indicate the interaction of a test sample with a peptide binding pair by a recognizable change in phenotype consequent to expression of the luciferase gene.

Defined Terms:

The term peptide binding pair refers to any pair of peptides having a known binding affinity for which the DNA sequence is known or can be deduced. The peptides of the peptide binding pair must exhibit preferential binding for each other over any components of the modified cell.

The term peptide as used in the above summary and herein means any peptide, polypeptide or protein, unless stated otherwise. As noted above, the peptides of a peptide binding pair can be a ligand and its corresponding receptor, or a ligand and any peptide having a known binding affinity for the ligand.

Heterologous as used in the above summary and herein means peptides which (1) are not expressed by the naturally-occurring host cell or (2) are expressed by the modified host cell by an expression method other than the expression method by which the host cell would normally express the peptide.

Unless specified otherwise, the term receptor as used herein encompasses the terms receptor, soluble receptor, transducer and binding protein. In preferred embodiments of the invention, the receptor employed is a receptor or soluble receptor, with receptor being more preferred.

Receptor as used herein means plasma membrane proteins that bind specific molecules, such as growth factors, hormones or neurotransmitters, and then transmits a signal to a cell interior, causing the cell to respond in a specific manner. This term includes single transmembrane proteins.

Soluble receptor means a non-transmembrane form of a receptor which is able to bind ligand. These are receptors released from a cell either by proteolysis or by alternatively spliced mRNA.

Binding protein means proteins that demonstrate binding affinity for specific ligand. Binding proteins may be produced from separate and distinct genes. For a given ligand, the binding proteins that are produced from specific genes are distinct from the ligand binding domain of the receptor, or its soluble receptor.

Transducer means a molecule that allows the conversion of one kind of signal into another, and the molecule is readily known as a transducer for one or more the peptides of a peptide binding pair, for example, a transducer for a ligand/receptor group.

BRIEF DESCRIPTION OF THE DRAWINGS

FIGS. 2A and 2B are photographs of plates which show the results of the growth experiments conducted in Example 1 for stains CY722, CY723, CY724, and CY781 on non-selective medium and selective medium, photographs A and B, respectively.

FIG. 5 is a graph representing the luciferase activity resulting from a protein-protein interaction between Kv4.3 and KChIP1 in recombinant yeast cells.

FIG. 6A is a photograph of media plates demonstrating that strain ybn66, which contains both fusion proteins, fails to grow on media containing cyclohexamide, which is indicative of a productive protein-protein interaction and CYH2 reporter gene activity.

FIG. 7A is a dose response curve demonstrating the ability of compound SBQ-1B3 to modulate luciferase activity resulting from a hKv4.3N-KChIP1 and Q205L/GaZ interaction.

FIG. 7B is a dose response curve demonstrating the ability of compound SBQ-3D10 to modulate luciferase activity resulting from a hKv4.3N-KChIP1 and Q205L/GaZ interaction.

DETAILED DESCRIPTION OF THE INVENTION

Figure 1:
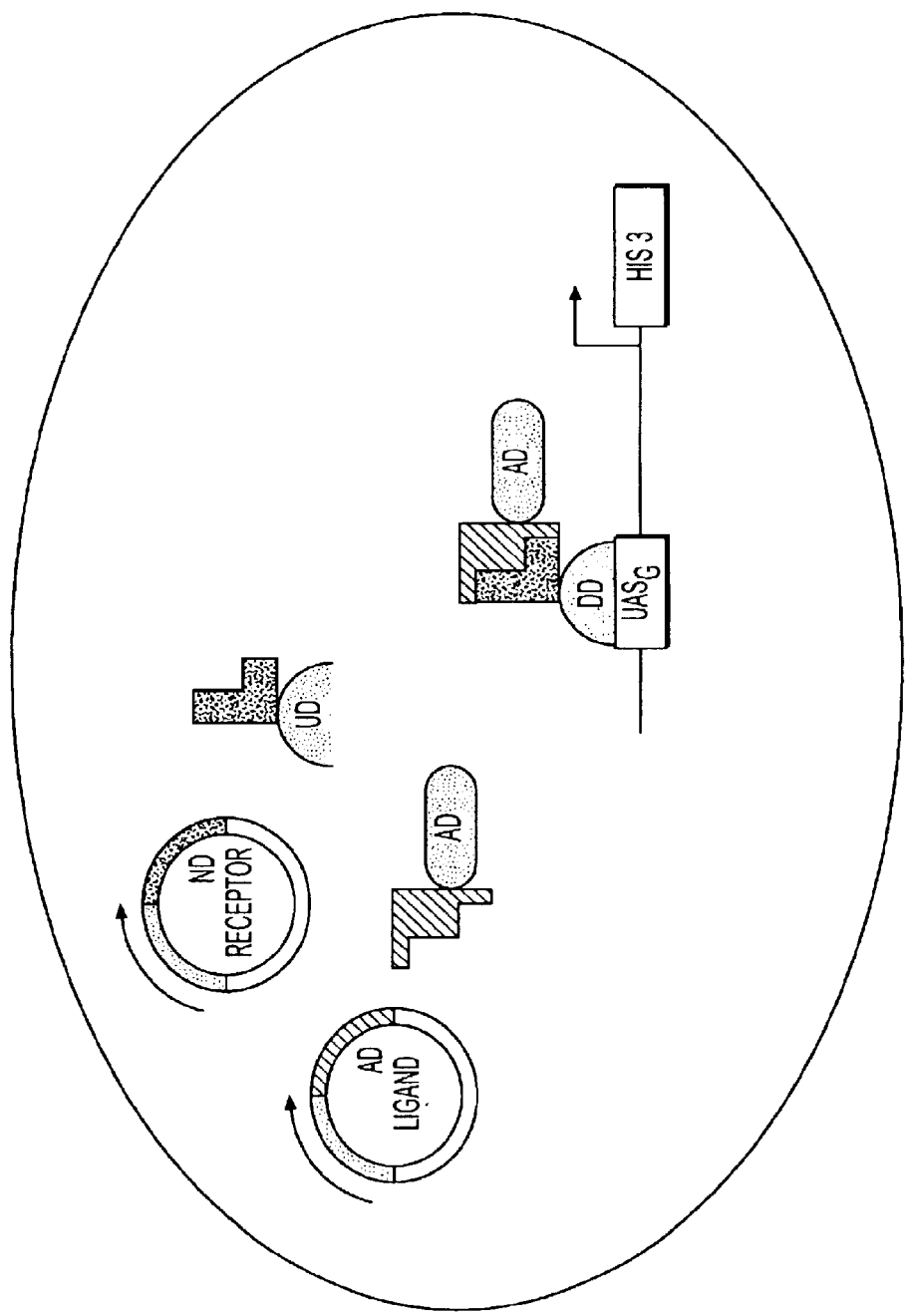
FIG. 1 is a schematic diagram of a cell which expresses, from separate plasmids, two heterologous fused proteins (one being the ligand fused to the activation domain of a transcriptional activation protein and the other fused protein being a receptor fused to the DNA binding domain of the transcriptional activation protein). The Figure shows the expression of the two fused proteins and the binding of the ligand and receptor, which brings together the binding domain and activation domain, reconstituting the transcriptional activation protein. Once the transcriptional activation protein is reconstituted and anchored by the DNA binding domain to the Upstream Activation Sequences (UAS) site, transcription of the reporter gene (HIS3) is initiated.

The modified cell of this invention employs a host cell. An effective host cell for use in the present invention simply requires that it is defined genetically in order to engineer the appropriate expression of heterologous fused proteins, reporter(s) and any other desired genetic manipulations. The host cell can be any eukaryotic cell, vertebrate or non-vertebrate. The host cell can be mammalian as well as amphibian, for example, a Xenopus egg cell. Preferably, the host cell is a fungal cell, for example, Aspergilla or Neuropora. In more preferred embodiments the host cell is a yeast cell. In alternatively preferred embodiments the yeast host cell is *Saccharomyces cerevisiae, Schizosaccharomyces pombe* or *Pichia pastoris*.

The modified host cell employs at least two genes for separately expressing the two heterologous fusion proteins. One of these fusion proteins comprises a first peptide of a peptide binding pair, or segment of said first peptide, which is joined to either a DNA binding domain or its corresponding transcriptional activation domain of a transcriptional activation protein. A second fusion protein comprises the second peptide of the peptide binding pair, or a segment thereof. The second peptide is fused to either a DNA binding domain or its corresponding transcriptional activation domain, whichever one is not employed in the first heterologous fused protein. The activity of the binding between the peptides of the peptide binding pairs is monitored by the use of a reporter gene, which is operatively associated with the transcriptional activation protein employed in the two fusion proteins.

The transcriptional activation protein can vary widely as long as the DNA binding domains and the activation domains are known or can be deduced by available scientific methods. The transcriptional activation protein can be any protein having two components, a DNA binding component and an activation component, wherein the transcriptional activation protein contains an acidic alpha helix for the activation of transcription. Preferably, the transcriptional activation protein is selected from Gal4, Gcn4, Hap1, Adr1, Swi5, Ste12, Mcm1, Yap1, Ace1, Ppr1, Arg81, Lac9, Qa1F, VP16, LexA, non-mammalian nuclear receptors, (for example, ecdysone), or mammalian nuclear receptors, (for example, estrogen, androgens, glucocorticoids, mineralocorticoids, retinoic acid and progesterone; see also Picard et al., 1990). Preferably, the transcriptional activation protein is a yeast protein, and more preferably, the transcriptional yeast protein is selected from Gal4, Gcn4 or Adr1. It is noted that any DNA binding protein can be used which functions with an activation domain. A DNA binding protein can be substituted for the DNA binding domain of a transcriptional activation protein if the recognition sequences operatively associated with the reporter gene are correspondingly engineered. Illustrative of non-yeast DNA binding proteins are mammalian steroid receptors and bacterial LexA (see Wilson et al., 1990).

The reporter gene is generally selected in order that the binding of the domains of the transcriptional activation protein can be monitored by well-known and straightforward techniques. Preferably, the reporter gene is selected based on its cost, ease of measuring its activity and low background, (that is, the activity can be determined at relatively low levels of expression of the reporter gene because of a high signal to background ratio and/or a relatively low or no uninduced activity). The reporter can be any reporter for which its activity can be detected by any means available. Illustrative of reporters which can be used in the present invention are reporter genes selected from the group of:

a) lacZ, Luciferase gene, green fluorescent protein gene, CAT;

b) genes complementing auxotrophies, such as HIS, URA, LEU, ARG, MET, ADE, LYS, TRP;

c) genes conferring antibiotic resistance, such as neo$^r$ and KAN; and d) genes conferring sensitivity to a chemical such as CYH2 or CAN1 (canavine resitance). In many embodiments it may be convenient for the reporter gene to prevent growth (CYH2).

Preferably, the activity of the reporter gene is indicated by calorimetric or fluorescent methods and/or by measuring growth of the yeast cell.

In a preferred embodiment, the reporter gene is a luciferase gene, for example, a luciferase gene from *Renilla reniformis* or *Photinus pyralis*. Luciferase genes from other organisms are well known to those of skill in the art. A significant advantage conferred by the use of the luciferase reporter gene for two-hybrid analysis is that it enables conversion of non-automated-agar diffusion based assays dependent on longer assay windows (days), to a liquid assay with much shorter assay windows (hours). Additionally, use of the luciferase reporter in yeast proves enhanced assay sensitivity over present formats, quantitative data, and enables assay automation, especially for higher throughput (384 well) assay formats. The utility of using this reporter system will be overall assay speed, ease, and the rapidness of reporter gene activity (thereby avoiding toxic false positives), and more simple data capture and processing, permitting easier quantification of data. The short assay time (4 hours) adds utility in drug screening applications in avoiding compound toxicity effects due to long (48+ hours) incubation times presently needed for standard autotrophic (HIS3, LYS2, URA3) reporters or counter selection (CAN1, URA3, CYH2) reporters, both of which require cell growth for endpoint determinations. The use of the luciferase reporter gene in yeast has application to two-hybrid-based systems.

As noted previously, the peptide employed in the modified cell is a peptide of a peptide binding pair for which the DNA sequence is known as well as the sequence of the second peptide of the binding pair. The peptides can also be peptides of a peptide binding complex which contains two or more peptides which bind each other to form the binding complex. The peptides of the peptide binding pair can be a specific ligand and a corresponding receptor or any other peptides which bind to each other preferentially, such subunits of an enzyme.

One of the significant advantages of this invention is the discovery that the modified cell employing the DNA binding and activation domains of a transcriptional protein can be used to monitor the binding of peptides of a peptide binding pair which bind through extracellular interaction. Certainly, if desired, peptides which bind through intracellular interaction can also be employed in any of the novel modified cells and methods of this invention. The peptide can be from a mammalian cell or non-mammalian cell. One of the most important embodiments of the present invention relates to the application of the novel modified cells and corresponding screening methods of this invention for studying numerous mammalian peptide interactions. The mammalian peptides include mammalian ligand/receptor interactions, such as hormone/receptor interactions. Illustrative of peptide hormones which can be used in the present invention are peptides selected from, but not limited to, one of the following groups: (a) cytokines, interleukins, hematopoietic growth factors, insulin, insulin-like growth factors, growth hormone, prolactin, interferons, and growth factors; (b) ligands for G-protein coupled receptors; (c) ligands for nonvertebrate receptors; (d) ligands for guanylyl cyclase receptors; and (e) ligands for tyrosine phosphatase receptors.

In alternative embodiments, the peptide is a growth factor selected from the group consisting of epidermal GF, nerve GF, leukemia inhibitory factor, fibroblast GF, platelet-derived GF, vascular endothelial GF, tumor necrosis factor, oncostatin M, ciliary neurotrophic factor, erythropoietin, steel factor, placental lactogen and transforming GF.

In various preferred embodiments, the peptide hormone is a ligand for a G-protein coupled receptor, such as growth hormone releasing factor, secretin, vasoactive inhibitory peptide, glucagon, thyrotropin, interleukin-8, luteinizing hormone (LH) or follicle stimulating hormone (FSH).

In additional alternative embodiments the peptide employed is a nonvertebrate peptide, such as those selected from the group consisting of plant system and insect differentiation peptides. However, in preferred embodiments, the peptide is selected from the group consisting of mammalian peptides, and more preferably, mammalian peptide hormones.

It is also noted that certain receptors may also be a peptide of a peptide binding pair or peptide binding complex. Illustrative of such receptors are those selected from one of the following groups: (a) a cell adhesion molecule; and (b) an immunomodulatory antigen recognition or presentation molecule or other related peptides. Illustrative of cell adhesion molecules are ICAM, VCAM, ECAM, fibronectin, integrin, selectin, and fibrinogen. Illustrative of an immunomodulatory, antigen recognition or presentation molecule are T cell receptor complex, B cell receptor complex, Fc receptors, major histocompatibility complex I, major histocompatibility complex II, CD4, CD8, CD27, CD30, and MAC complex.

It is also noted that specific types of transducers may also be a peptide of a peptide binding pair or peptide binding complex. The transducer proteins employed can be any transducer protein which binds at least one of the peptides of the peptide binding pair or peptide binding complex. Transducer proteins include gp130, kh97, AIC2A, and AIC2B.

Preferably, the heterologous fused proteins are expressed by transformation of the yeast cell with an autonomously-replicating plasmid capable of expressing the fusion protein, although, alternatively, they can be expressed by chromosomal modification.

As noted, the screening methods of this invention are designed in order to detect the ability of a test sample to affect the binding of a peptide binding pair, for example, ligand-receptor interaction. Basically, the method comprises determining the activity of the reporter gene upon adding a test sample to a modified host cell of the present invention under conditions suitable to detect the activity in the presence of a sample or under a condition for which the modified host cell exhibits such activity only in the presence of a sample having binding interaction with the peptide binding pair. Preferably, the activity of the reporter gene is determined by measuring a change in a selected phenotype which directly correlates to activity of the reporter.

The novel modified cells of this invention are readily applied in various screening methods for determining the binding ability of a test sample. The test sample may be a peptide, which is preferably about two amino acids in length, or a non-peptide chemical compound. The non-peptide test sample includes compounds, complexes and salts as well as natural product samples, such as plant extracts and materials obtained from fermentation broths. The modified host cells are cultured under suitable conditions for growth to study the interaction of a test sample on the binding interaction of the peptide binding pair. The modified host cells are placed in a growth medium, which preferably contains agar, with the test sample applied to the surface of the growth medium. The growth medium is preferably a conventional liquid medium of growth reagents and water, such as yeast synthetic medium (YSM available from BIO101 (also see Rose et al., *Methods in Yeast Genetics*, 1990)).

One of the embodiments of the present invention is directed to a novel modified host cell and screening method which indicate the interaction of a test compound with a selected peptide binding pair by a recognizable change in phenotype. This modified host cell exhibits the change in phenotype only in the presence of test compound having binding affinity for one of the peptides of the peptide binding pair. This host cell is referred to herein as a "rescue" system. Normally, a cell response is exhibited when the two domains of the transcriptional activation protein interact. However, in a rescue system a positive indication of change in the phenotype does not occur when the two domains of the transcriptional activation protein interact. A positive indication of change in the phenotype occurs only when a test sample interrupts the interaction of the two domains of the transcriptional activation protein. In a rescue system, a modified host cell is capable of expressing at least two heterologous fusion proteins. Further, the host cell comprises a reporter gene operatively associated with the transcriptional activation protein, wherein said reporter gene prevents the exhibition of a specific phenotype on a selective medium due to the expression of the transcriptional activation protein or a portion thereof. A mutation in the chromosomal DNA of the host cell allows for reversal of the detectable phenotype on the selective medium in the absence of expression of the reporter gene. If needed, there is a deletion or mutation in the chromosomal DNA of the host cell for a transcriptional activation protein in order that transcriptional activation only occurs upon productive interaction of the selected binding pair. Only when a test sample interrupts the interaction of the two domains of the transcriptional activation protein will the modified cell grow or survive, or exhibit another selected phenotype. Preferably, the phenotype corresponds to the growth of the cell.

Once a screening method, as discussed above, is used to determine whether a test sample interacts with, or rather disrupts, the peptide binding observed in the absence of a test sample, a secondary screen is employed to determine the specific binding affinity of the test sample, that is, to which peptide of the peptide binding pair the test sample binds. The secondary screen employs the novel cells of this invention wherein cells are adapted to exhibit a phenotype or phenotypic change only in the presence of a test sample which binds one peptide of the peptide binding pair. One of the preferred methods for determining the specific binding characteristics of the test sample involves employing cells which contain an effective (relatively high) copy number of either fusion protein containing one of the peptides. An effective copy number is any copy number sufficient to enable determination of the specific binding of the test sample. Preferably, the gene copy number is at least about 5, and preferably ranges from about 5 to about 50, with higher copy numbers being the most preferred. The other fusion protein is maintained at a relatively low (1 to about 2 copies per cell) by either integration into a cell chromosome or by utilizing chromosomal centromeric sequences on the expression plasmid. If a high copy number of a first peptide is used in a cell of this invention, the cell will be more sensitive to the presence of the test sample which binds the second peptide of the peptide binding pair since the limiting amount of second peptide determines the level of the activity of the reporter gene, that is, the change in phenotype observed. Conversely, if a high copy number of a gene encoding the second peptide of a peptide binding pair is used, the cell will be more sensitive to the presence of a test sample which binds the first peptide since the limiting amount of the second peptide determines the level of the activity of the reporter gene, that is, the change in phenotype observed. A direct comparison of the effects of a test compound on the phenotypes of the two strains (receptor>>>ligand versus ligand>>>receptor) demonstrates the specific protein interaction of the compound. As discussed above, the genes expressing the peptides, as well as the reporter gene, are preferably expressed by transformation of the host cell with an autonomously-replicating plasmid.

An additional modified host cell of this invention is directed to cells which can be used to study peptides ligands which employ dual receptors or a receptor and a transducer for activation or transmission of a signal from the binding of multiple peptide binding components, that is, three or more peptide binding components.

Receptor dimerization is a critical first step for signal transduction for certain classes of receptors. Dimer receptor structures can be composed of identical receptor units, (for example, insulin receptor, IGF-I receptor, PDGF receptor, kinase inert domain receptor (KDR), or colony stimulating factor (CSF)-I receptor). Alternatively, they can be comprised of non-identical receptor units, (for example, IL-6R+ gp130, insulin-IGF-I hybrid receptor, LIF+gp130, CNTF+ gp130, or various interferon receptors).

The components of a modified host cell for monitoring the binding activity of a peptide having a "dual receptor" system are as follows: the gene sequence (a) is a gene sequence encoding a heterologous fusion protein; said fusion protein comprising one peptide of a multiple peptide binding complex, or segment of said peptide, which is joined to either a DNA binding domain or its corresponding transcriptional activation domain of a transcriptional activation protein; and the gene sequence (b) is a gene sequence encoding a heterologous fusion protein; said fusion protein comprising a second peptide of said multiple peptide binding complex, or a segment of said receptor, fused to either a DNA binding domain or its corresponding transcriptional activation domain, whichever one is not employed in (a). The modified host cell for studying a multiple peptide binding complex, such as a dual receptor system, also comprises an appropriate reporter gene and chromosomal mutations for specific analysis of the peptide (ligand/receptor) interaction as discussed infra. One can express a third peptide (e.g. a ligand) to establish a control for comparative or competitive testing.

As noted above, for the study of multiple binding peptide complexes, i.e. higher-order proteins which contain three or more peptides, one can actually use the modified host cell of the present invention to express three or more peptides. In the case of a tripeptide binding complex, any two of the peptides can be fused to the two components of the transcriptional activation protein. For example, to study the interaction of a ligand which interacts via receptor dimerization, one can express the receptors as fused proteins with the ligand being expressed as a nonfusion protein. This host cell system can be also be applied in studying multi-protein enzyme complexes. For any multipeptide binding complex, one can identify novel peptides which interact with the complex by expressing novel proteins from random complementary DNA sequences, for example, a cDNA library, fused to one of the domains of a transcriptional activation protein. In such a system, one of the known peptides of the peptide binding complex is fused to the other domain of the transcriptional activation protein while other units of the peptide binding complex are expressed as nonfusion peptides. It is further noted that the number of peptides expressed by the modified host cell should only be limited by the available detection means and the capacity of the host cell.

The novel screening methods can be utilized to identify compounds interacting with any peptide binding pair, for example, any receptor and/or ligand. Also, this modified cell system with a reporter gene to create a screen can be applied to any protein-protein interaction to discover novel compounds that disrupt that interaction. As specific examples: a) protein kinases implicated in cancers can be inserted into the system to rapidly screen for novel compounds that block the kinase-target interaction and thus may serve as unique cancer therapeutics; b) viral coat proteins, such as human immunodeficiency virus glycoproteins, and corresponding cell surface receptor proteins, such as CD4, can be inserted into the system to rapidly screen for compounds that disrupt this interaction, and may serve as anti-viral agents; and c) the two subunits for the Plasmodium ribonucleotide reductase enzyme can be expressed in the system to screen for compounds which prevent this specific protein association and thus may serve as novel anti-malarial agents.

The following Examples are provided to further illustrate various aspects of the present invention. They are not to be construed as limiting the invention.

EXAMPLE 1

Specific and Reversible Ligand-Receptor Interaction

Genes encoding fusion proteins are generated by cloning growth hormone (GH) and growth hormone receptor (GHR) cDNA sequences into plasmids containing the coding region for the domains of Gal4. DNA binding domain (Gal4) fusions are constructed in pAS2, which is described in Wade Harper et al. Gene activation domain (Gal4) fusions are constructed in pACT-II, which is identical to pACT (described in Durfee et al., 1993) except with a modification of the polylinker region. Into the Bgl II site is added the following sequence: Bgl II-Hemagglutinin epitope-NdeI-NcoI-SmaI-BamHI-EcoRI-XhoI-Bgl II, as adapted from the polylinker sequence of pAS2 (Wade Harper et al., 1993). The cDNA encoding the mature peptide for porcine GH is generated using standard polymerase chain reaction (PCR) techniques (see Finney, 1993).

Oligonucleotides prepared on an ABI oligosynthesizer are designed according to the published cDNA sequence for pig GH (see Su and El-Gewely, 1988). A 30 base 5' oligonucleotide contains a NcoI site (5'-CATGCCATGGAGGCCTTCCCAGCCATGCCC 3') (SEQ ID NO: 1) and a 27 base 3' oligonucleotide contains a BamHI site (5'-CGGGATCCGCAACTAG-AAGGCACAGCT-3') (SEQ ID NO: 2). The GH cDNA is generated using a pig pituitary lambda gt11 library as template source. A 540 bp fragment is obtained, ligated into pCR II vector (Invitrogen Corp.), recombinants are confirmed by restriction enzyme digest, and the DNA produced as described in Maniatus et al., 1982. The cDNA sequence is confirmed by di-deoxy terminator reaction using reagents and protocols from Perkin-Elmer Cetus Corp. and an ABI 373A automated sequencer. The GH cDNA is directionally cloned into pACT-II via NcoI and BamHI sites. The CDNA encoding the extracellular domain of the GHR is generated using standard PCR methods. A 33 base 5' oligonucleotide containing a NcoI site (5'-CATGCCAT-GGAGATGTTTCCTGGMGTGGGGCT-3') (SEQ ID NO: 3) and a 39 base 3' oligonucleotide containing a termination codon, followed by a NcoI site (5'-CATGCC-ATGGCCTACCGGAAATCTTCTTCACATGCTGCC-3') (SEQ ID NO: 4) are used to generate a 742 bp fragment encoding amino acids 1–247 of the rat GHR (Baumbach et al., 1989). This GHR cDNA is cloned into vector pCRII as previously described above, and then subcloned into the NcoI site of vector pAS2. DNA of the final recombinant vectors is transformed into yeast strain(s) by the lithium acetate method (Rose et al., 1990).

A yeast host (Y190) containing a $UAS_{GAL}$-HIS reporter gene is prepared according to the procedure described in Wade Harper et al., 1993. The genotype of strain Y190 is MATa leu2-3, 112 ura3-52 trp1-901 his3d200 ade2-101 gal4 gal80 URA3::GAL-lacZ LYS2::GAL-HIS3 cyh$^r$. Strain Y190 is transformed with both fusion constructs or with a single fusion construct plus the opposing vector containing no heterologous sequences. All strains are found to exhibit equal growth on nonselective medium (FIG. 2A). These strains are then tested for growth on selective medium, that is, a growth medium lacking an amino acid which is synthesized by activation of the reporter gene. Only the strain containing both hybrid proteins (CY722) is able to grow, while the strains containing either the ligand or receptor fusion alone do not grow (CY724 and CY723, respectively; FIG. 2B). Two independent samples of each strain are streaked on synthetic medium containing 2% glucose, yeast nitrogen base, ammonium sulfate, 0.1 mM adenine and 60 mM 3-amino-triazole (plate B) or on the same medium supplemented with histidine (plate A). Plate A is incubated at 30 C. for three days; plate B for five days. These results demonstrate that GH and GHR can mediate the Gal4-dependent activation of the reporter gene in an interaction suggestive of ligand-receptor binding.

EXAMPLE 1A

Competing Expressed Free Ligand (GH) in the Presence of GH and GHR Fusion Proteins To substantiate the apparent binding of GH to its receptor in the foreign environment of a yeast nucleus, the system is modified to add a third plasmid mediating expression of "free" ligand to show that the GH peptide competes with the GH-Gal4 fusion protein, reversing the 2-hybrid interaction shown in Example 1. The parental strain Y190 (Wade Harper et al., 1993) is grown on a medium containing 5-fluoro-orotic acid to select for derivatives that spontaneously lose the URA3 gene (see Rose et al., 1990). The resultant strain, designated CY770, is utilized for all experiments examining the effects of protein expressed concurrently from the third component, (that is, the third plasmid). The cDNA encoding GH is generated by PCR methods using a 38 base 5' oligonucleotide containing an EcoRI site (5'-CCGMTTCAAAATGGCCTTCCCAGCCATG-CCCTTGTCC-3') (SEQ ID NO: 5) and a 26 base 3' oligonucleotide containing a HindIII site (5' CCAAGCTTCAACTAGAAGGCACAGCT-3') (SEQ ID NO: 6) for subsequent subcloning into the vector pCUP. pCUP is an inducible yeast expression vector derived from pRS316 (Hill et al., 1986). Briefly, this vector is constructed by inserting the 3' end of the yeast PGK gene (from PPGK; Kang et al., 1990) into the pRS316 cloning region as a BamHI-SalI fragment to serve as a transcriptional terminator. To this plasmid, the CUP1 promoter region (Butt et al., 1984) is amplified by PCR as a SacI-EcoRI fragment and inserted into corresponding sites of the plasmid to create pCUP. The GH expression plasmid (GH-pCUP) is then co-transformed with the GH and GHR fusion constructs into strain CY770 to generate CY781. Concurrent expression of free GH with the GH and GHR fusion proteins (CY781) is shown to block GH-GHR-dependent cell growth on selective medium (FIG. 2B). This experiment typifies an in vivo competition assay and demonstrates the reversibility of the observed ligand-receptor interaction.

EXAMPLE 1B

Binding of Peptide Hormone Prolactin (PRL) and its Receptor

To expand and validate this technology, a similar system was developed using the peptide hormone prolactin (PRL) and its receptor. Prolactin is structurally related to GH and the prolactin receptor (PRLR) is also a member of the cytokine receptor superfamily. Unlike human GH, subprimate GH does not readily bind the PRLR (Young and Bazer, 1989); nor does PRL readily bind the GHR (Leung et al., 1987). Mature porcine PRL is generated as a fusion to the GAL4 activation domain. Oligonucleotides are designed to pig PRL (obtained from GenBank; Accessign No. X14068), and used to generate the mature pig PRL protein hormone from a pig pituitary lambda gt11 library, using standard PCR methods. A 31 base 5' oligonucleotide includes an EcoRI site (5'-CGGAATT-CTGCCCATCTGCCCCAGCGGGCCT-3') (SEQ ID NO: 7) and corresponds to sequences encoding amino acids 1–7. A 30 base 3' oligonucleotide contains an EcoRI site (5'-GAATTCACGTGGGCTTAGCAGTTGCTGTCG-3') (SEQ ID NO: 8) and corresponds to a region of cDNA 3' to the endogenous termination codon. A 600 bp fragment is obtained, ligated into vector pCR 11, and confirmed by restriction enzyme digest and sequence analysis. The PRL cDNA is cloned into pACT-II via the EcoRI site.

The extracellular domain of the porcine PRL receptor (PRLR) is generated as a fusion to GAL4 DNA binding domain. Oligonucleotides are designed based on sequence of the mouse PRLR (Davis and Linzer, 1989) A 31 base 5' oligonucleotide contains a SmaI site (5'-TCCCCCGGGGATGTCATCTGCACTTGCTTAC-3') (SEQ ID NO: 9) while the 31 base 3' oligonucleotide contains a termination codon followed by a SalI site (5' TCCGTCGACGGTCTTTCAAGGTGAAGTCATT-3') (SEQ ID NO: 10). These oligonucleotides flank the extracellular domain of the PRLR, encoding amino acids 1–229. A pig pituitary lambda gt11 library is used as a template source. Using standard PCR methods, a 687 bp fragment is generated, ligated into pCRII, and the nucleotide sequence is confirmed. The PRLR cDNA is cloned into the pAS2 vector via the SmaI and SalI restriction sites.

Strain Y190 was transformed with the PRL or PRLR fusion expression plasmids either alone (CY727 or CY728, respectively) or together (CY726). Cells expressing both the PRL and PRLR fusions are able to grow on selective medium while the strains containing either the ligand or receptor fusion alone can not. These results mirror those observed in the GH-GHR system in the examples above and establish the general utility of the 2-hybrid system for examination of ligand binding to members of this receptor superfamily.

EXAMPLE 1C

Additional Confirmation of Ligand-Receptor Specificity for the Novel Yeast Host Cell System Additional strains are developed to assess ligand-receptor specificity. URA-strains expressing GH and GHR fusion proteins are transformed with pCUP or PRL-pCUP, while strains expressing PRL and PRLR fusion proteins are transformed with pCUP, or PRL-pCUP. Briefly, PRL-pCUP is constructed in a fashion similar to that described for GH-pCUP. The PRL cDNA is generated by PCR using a 33 base 5' oligonucleotide with an EcoRI site (5'-GAATTCAAAATGCTGCCCATCTGCCCCAGCGGG-3') (SEQ ID NO: 11) and the 3' oligonucleotide in example 1B. The resulting fragment is introduced into pCUP via the EcoRI site. As demonstrated in the above Examples, a strain expressing the GH and GHR fusions with no competitor grows on selective medium and this growth is abolished with coexpression of free GH. The prolactin experiment produces similar results, which confirms the specificity of the ligand-receptor binding in the yeast cell. A strain carrying PRL and PRLR fusions (CY787) can grow on selective medium and this growth is abrogated by expression of free PRL (CY786: Table 1).

To test selectivity of the GHR, a strain containing the GH and GHR fusions is transformed with PRL-pCUP. This strain grows on selective medium (CY785; Table 1). These data indicate that GH binding to its receptor in this system can be efficiently competed by excess GH (CY751) binding but not by the related PRL peptide (CY755). The results from the above experiments, expressing three heterologous proteins, illustrates the specificity of ligand-receptor interaction(s) in the system of this invention.

TABLE 1

Strain list and bioassay results[a]

| Designation | AD fusion[b] | BD fusion[c] | pCUP[d] | Growth[e] |
|---|---|---|---|---|
| CY700 | — | — | — | 0 |
| CY722 | GH | GHR | — | + |
| CY723 | vector | GHR | — | 0 |
| CY724 | GH | vector | — | 0 |
| CY726 | PRL | PRLR | — | + |
| CY770 | — | — | — | 0 |
| CY781 | GH | GHR | GH | 0 |

TABLE 1-continued

Strain list and bioassay results[a]

| Designation | AD fusion[b] | BD fusion[c] | pCUP[d] | Growth[e] |
|---|---|---|---|---|
| CY784 | GH | GHR | vector | + |
| CY785 | GH | GHR | PRL | + |
| CY786 | PRL | PRLR | PRL | 0 |
| CY787 | PRL | PRLR | vector | + |

[a]All yeast strains are derived from strain Y190 (Wade Harper et al. 1993). The genotype is MATa gal4 gal80 his3 trp1-901 ade2-101 ura3-52 leu2-3, 112 URA3::GAL-lacZ LYS2::GAL-HIS3 cyh. Strains with number designations equal to or greater than 770 do not have the URA3::GAL-lacZ gene. A dash indicates that a strain does not contain the denoted plasmid.
[b]AD fusions are pACT derivatives; GH or PRL fused to the Gal4 activation domain.
[c]BD fusions are pAS2 derivatives; extracellular domains of GH or PRL receptors fused to the DNA binding domain of Gal4.
[d]pCUP denotes peptides expressed from the pCUP plasmid.
[e]Summary of bioassay results. Each strain is grown on selective medium for 3 to 5 days at 30 C. then scored for cell growth, indicated by a plus.

EXAMPLE 2

Screen for Compounds Disrupting Ligand-receptor Interaction

Low-copy-number plasmids expressing GHR- or GH-Gal4 fusion proteins (pOZ153 and pOZ152, respectively) are constructed to reduce expression of these proteins. In addition, a novel reporter gene is constructed that prevents cell proliferation on selective medium unless expression is abrogated. To construct the GHR fusion expression plasmid, a SacI-BamHI restriction fragment containing a yeast constitutive promoter and GAL4 sequences is isolated from pAS1 (Durfee et al., 1993) and cloned into pUN30 (Elledge and Davis, 1988). The extracellular domain of GHR is then fused to GAL4 by ligation as an NcoI fragment as described in Example 1 to create pOZ153. To construct the GH fusion expression construct the entire GH-Gal4 region With promoter and terminator sequences is isolated from the plasmid described in Example 1 as a PvuI-SalI fragment. This DNA segment is cloned into pUN100 (Elledge and Davis, 1988) generating pOZ152. A reporter gene is constructed by isolating the yeast CYH2 coding region and operatively linking it to a GAL promoter in a yeast expression plasmid. Briefly, the GAL1 promoter region is inserted into YEp352 (Hill et a/., 1986) as a 685 bp EcoRI-BamHI fragment. CYH2 sequences are amplified by PCR using oligonucleotides primers (5'-GGATCCMTCMGAATGCCTTCCAGAT-3' (SEQ ID NO: 12) and 5'-GCATGCGTCATAGAAATMTACAG-3' (SEQ ID NO: 13)) and pAS2 as the template. The PCR product is digested with BamHI plus SphI and cloned into the corresponding sites in the YEp352-GAL vector. These plasmids are transformed into yeast strain CY770 which carries a mutation at the chromosomal cyh2 gene rendering the strain resistant to the protein synthesis inhibitor cycloheximide. The presence of all three plasmids is necessary to confer cycloheximide sensitivity (cyh$^s$).

The strain (CY857) containing the ligand and receptor fusion plasmids plus the reporter plasmid forms the basis of a simple primary screen for compounds that disrupt the binding of GH to its receptor. Strain CY857 is embedded in standard yeast growth medium containing 10.0 ig/ml cycloheximide. Due to the ligand/receptor interaction driving expression of the CYH2 reporter gene, the strain is cyh$^s$ and thus unable to grow. Chemical compounds are placed on this test medium. Compounds which impair GH-GHR binding are identified by the growth of cells surrounding the compound because in the absence of CYH2 expression the cells become resistant to cycloheximide present in the medium.

Secondary Screen to Determine Target of Sample

Disruption of ligand-receptor binding in this assay can result from reaction of the compound with either the receptor or ligand fusion component. The specific target of the novel compound is determined by a simple secondary assay utilizing strains overexpressing one of the fusion proteins. Strain CY858 expresses the GHR-GAL4 fusion in large excess due to the construct being maintained within the cells at high copy number (pOZ149), while the GH-fusion (pOZ152) is maintained at levels similar to the base strain (CY857). Conversely, strain CY859 expresses the GH-GAL4 fusion in large excess due to this construct being maintained within the cells at high copy number (pKY14), while the GHR fusion (pOZ153) is maintained at levels similar to base strain (CY857). Compounds rescuing growth in the primary screen using CY857 (GH and GHR fusions expressed on low copy numbers plasmids) are then assayed in the same manner using CY858 (GHR>>GH) or CY859 (GH>>GHR) as the test strain. For example, when ligand-receptor binding is inhibited by a compound reacting with the GHR, the secondary screen will demonstrate a detectable change for the phenotype measured. secondary testing of the rescuing compound on strain CY858 which overexpresses the GHR fusion produces a smaller growth in the presence of the compound than that observed for CY859. This detectable change in the measured phenotype occurs because the overabundance of GHR titrates the compound thereby increasing CYH2 expression and inhibiting cell growth. CY859 produces a detectable change similar to CY857 because the GHR fusion protein is limiting. A compound interacting with the ligand fusion demonstrates the inverse change in measured phenotype in this secondary assay.

EXAMPLE 3

Demonstration of Ligand Dependent Receptor Dimerization

Multiple protein interactions (for example; ligand-receptor-receptor) are investigated with the expanded system which expresses a third protein using the following scheme.

Figure 3:
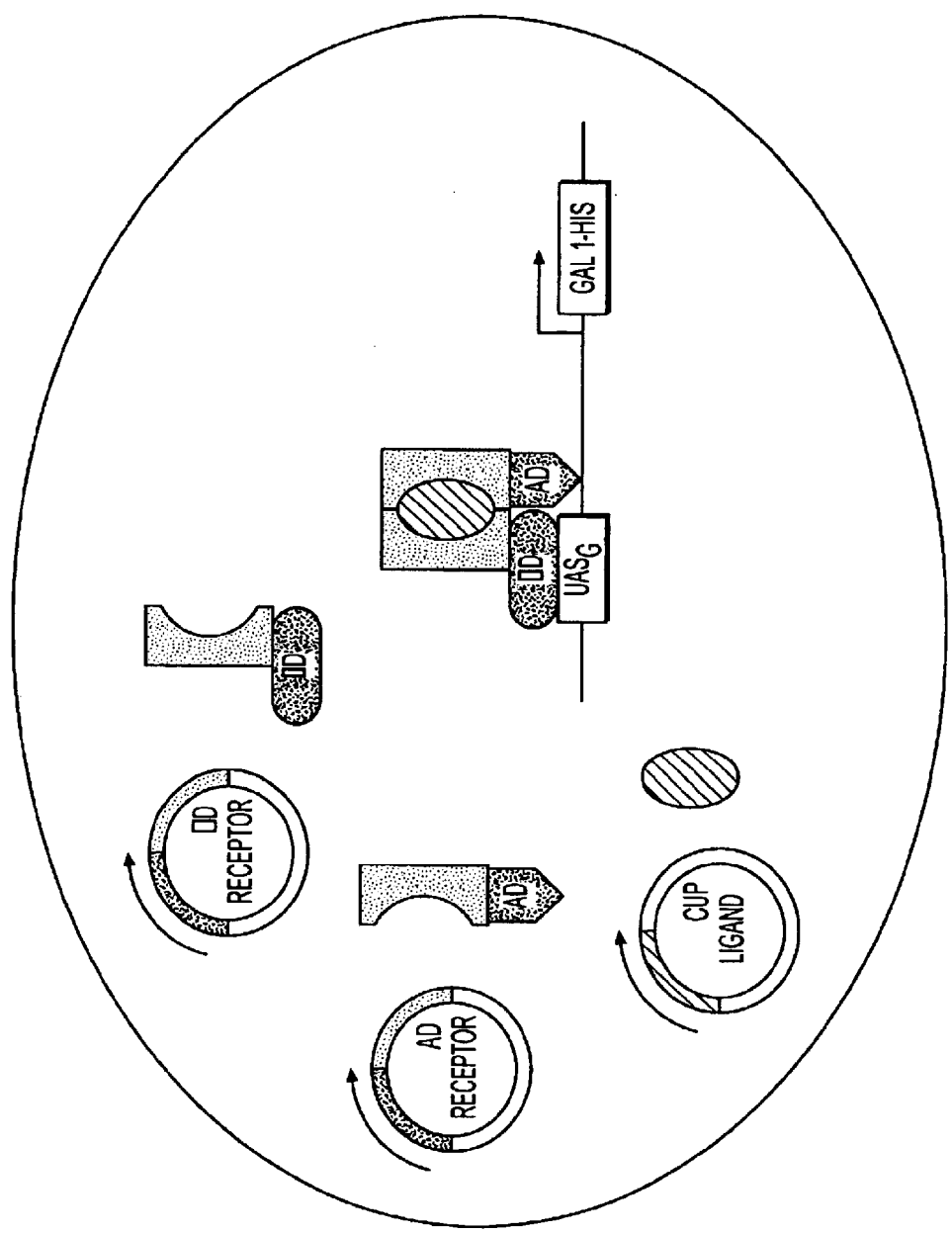
FIG. 3 is a schematic diagram of a dimer model, in which the ligand binds to a dual receptor system. The schematic diagram depicts a cell which expresses proteins from three separate plasmids. Two heterologous fused proteins (one fused protein being a first receptor fused to the activation domain of a transcriptional activation protein and the other fused protein being a second receptor fused to the DNA binding domain of the transcriptional activation protein) are expressed and free ligand, (that is, ligand which is not fused to either of the two domains of the transcriptional activation protein), is expressed from a third plasmid. The figure shows the expression of the two fused proteins and the binding of the free ligand and two receptor fusions which brings together the binding domain and activation domain, reconstituting the transcriptional activation protein. Once the transcriptional activation protein is reconstituted and anchored by the DNA binding domain to the Upstream Activation Sequences (UAS) site, transcription of the reporter gene (HIS3) is initiated.

One unit of the receptor dimer is generated as a fusion protein with either the Gal 4 DNA binding or activation domain. The other unit of the receptor dimer is generated as a fusion protein with corresponding Gal DNA binding or activation domain, whichever is not used for the first fusion. The gene encoding the ligand is expressed from the third plasmid and is produced as a free (non-fusion) ligand. Interaction of the fusion proteins occurs only in the presence of ligand (see FIG. 3).

The interaction of vascular endothelial cell growth factor (VEGF) with the ligand binding domain of its cognate receptor (KDR, kinase insert domain containing receptor) is described as an example for this system. KDR is a tyrosine kinase receptor, and dimer formation (1 ligand-2 receptors) is suggested to be important for hormone-induced receptor function. The cDNA encoding the ligand domain of KDR (Terman et al., 1991) is isolated as an NCO I-BamHI fragment and cloned into both the pACT-II and pAS2 vectors. The cDNA encoding the mature protein for VEGF is generated using standard PCR techniques. Oligonucleotides are designed from published sequence (see Fischer et al., 1991). A 34 base 5' oligonucleotide containing an EcoRI site (5'-CGGMTTCGMGTATGGCACCCATGG-CAGMGGA-3') (SEQ ID NO: 14) and a 28 base 3' oligonucleotide containing an EcoRI site (5'-CGGMTTCGGATCC- TCATTCATTCATCA-3') (SEQ ID NO: 15) are used to generate a 450 bp fragment encoding the mature protein and cloned into the EcoRI site of pCUP. DNA of final recombinant vectors is transformed into yeast by the lithium acetate method to generate appropriate strains.

Figure 4:
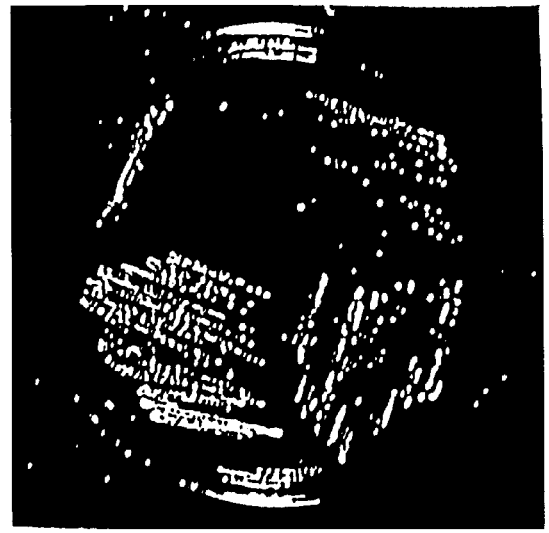
FIG. 4 is a photograph of the growth plate obtained for strains CY846 and CY847 from Example 3, showing ligand-dependent stimulation of receptor dimerization.

The yeast host strain (CY770) is transformed with KDR-pACT-II, KDR-pAS2 and VEGF-pCUP to generate strain CY846; or transformed with both receptor fusions and pCUP to generate strain CY847. Additionally, both KDR-pACT-II and KDR-pAS2 are transformed together (CY845) or separately (CY843 or CY844) or VEGF-PCUP alone (CY841) as control strains. Strains are tested for growth on selective medium. The strain (CY846) that expresses the VEGF ligand plus the two receptor fusion proteins exhibits substantial growth on selective media in comparison to the strain CY847, which does not express the VEGF ligand (see FIG. 4). These results demonstrate that the effective cells of this invention can be used to study ligand-dependent dimerization of the receptor.

EXAMPLE 4

Screen for Compounds that Act as Ligands in a Dimer Receptor System

Dimerization (oligomerization) of receptor units is often an important first step in activation of receptors such as those for the growth factors, cytokines, and those described above. The novel cell system described in Example 3 can be applied to the discovery of novel compounds which promote (or block) receptor dimerization. Such novel interacting compounds may serve as effective therapeutic agents for pathologies associated with these receptors.

Plasmids expressing the dimer receptor unit(s) as fusion proteins are generated as discussed in Example 3. The strain (CY845) containing the KDR-pACT-II and KDR-pAS2 fusions serves as an example of a simple primary screen for receptors which exhibit a dimer structure. Strain CY845 is embedded in synthetic agar medium deficient in histidine (Rose et al., 1990). Test compounds are applied to the top of this test medium. Chemical compounds which induce interaction of the two receptor fusions (in the absence of ligand) results in the reconstitution of the endogenous transcriptional activator, which is linked to a reporter gene, such as HIS3. The reconstitution is identified by growth of cells surrounding the compound.

EXAMPLE 5

Generation of Yeast Two-hybrid Strains for Kv4.3 and KChIP1 Interaction

The interaction between the N-terminus of the potassium channel 4.3 (hKv4.3N) and a previously described interacting protein, KChIP1, was used to test the Gal-luciferase reporter (Kp126; cloning described below) for yeast two-hybrid applications. The plasmids hKv4.3N-pGBT9 and KChIP1-pACT2 are described in An et al., (2000), and are used to generate appropriate test and control yeast strains for two-hybrid analysis. Yeast strains were transformed using a lithium acetate procedure and plated on appropriate media (Rose et al., 1990) All yeast media and reagents are prepared using standard methods. Plasmids hKv4.3N-pGBT9, KChIP1-pACT2 and Kp126 [Gal-luciferase] were transformed into yeast strain CY770 (described in U.S. Pat. No. 5,989,808; Ozenberger and Young, 1995) to generate interaction strain KY140. Plasmids pGBT9, KChIP1-pACT2 and Kp126 were transformed into yeast strain CY770 to generate control strain KY142. Plasmids hKv4.3N-pGBT9, pACT2 and Kp126 were co-transformed into yeast strain CY770 to generate control strain KY143. Plasmids pGBT9, pACT2, and Kp126 were co-transformed into yeast strain CY770 to generate control strain KY144.

The luciferase reporter plasmid(s) for use in yeast two-hybrid applications were generated as follows. Plasmid pEK1 (described in Price et al., 1995) was digested with BamHI+SalI restriction enzymes, dephosphorylated, and gel purified. The luciferase coding region was obtained as a Bgl II-Sal I 1.9 kb cDNA fragment from pGL3Basic (Promega), purified, and ligated to the prepared pEK1 vector using standard procedures to generated plasmid Kp126. The recombinant DNA is transformed into DH5α $E.\ coli$ using standard procedures and plasmid DNA prepared. The construct was confirmed by restriction enzyme analysis and cDNA sequence analysis (using primer Kx38: 5'-TCAMTTMCMCCATAGGAT-3') (SEQ ID NO: 16). Kp126 was used extensively for yeast two-hybrid systems and retains the original mammalian Kozak sequence from original DNA source.

A low copy number (CEN) version of this reporter was generated. The URA3 marked pRS416 vector (Stratagene) was digested with SmaI, dephosphorylated, gel-isolated and purified. The Gal1/10p-Luciferase cassette was obtained from Kp126 by digestion with EcoRI+MluI to generate a 3.5 kb fragment containing promoter, luciferase ORF and ste7 terminus. The CDNA fragment was blunt-ended, gel-isolated and purified and ligated into the prepared pRS416 vector to generate the resultant recombinant plasmid Kp132. Plasmid Kp132 was transformed into bacterial cells and DNA was prepared and confirmed by restriction analysis. In addition, a TRP1 marked version of the CEN luciferase plasmid Kp132 was generated. A MluI fragment containing the Gal1/10-luciferase-STE7 term cassette from Kp126 was obtained, blunt ended and ligated into an appropriately prepared pRS414 backbone to generate plasmid Kp137. This recombinant plasmid was transformed into bacterial cells, and DNA was prepared using standard techniques.

To evaluate the two-hybrid interaction of the hKv4.3N and KChIP1 fusion proteins, luciferase assays were performed. Briefly, colonies were inoculated in 3 mls SC-, -leucine, -tryptophan-uracil yeast medium and grown overnight at 30° C. Cell density was measured at $OD_{600}$ and densities were adjusted to an $OD_{600}$ of 0.2. Cells are seeded in 96-well plates (100 ul) and grown for an additional 2–3 hrs. Luciferase substrate (LucLite, Packard) was added (100 ul), and the plate was incubated for 50 minutes, in the dark at room temperature, while shaking.

Luciferase activity was determined using a 2 second read on a TopCount luminometer (Packard).

An increase of approximately 47 to 50-fold in luciferase signal was observed from this reporter in the yeast two-hybrid system for the productive protein-protein interaction of Kv4.3N-pGBT9 and (1 v)KChIP1-pACT2 in yeast strain KY140; in comparison to appropriate negative control yeast strains containing only one fusion protein and an empty vector (strains KY142, KY143), or two empty vectors (KY144) (See FIG. 5; right side).

Analogous yeast strains were generated using 4.3N-pGBT7 and KChIP1-pACT2 with a low copy number version of the Gal-luciferase reporter (Kp132). Plasmids hKv4.3N-pGBT9, KChIP1-pACT2 and Kp132 [CEN based Gal-luciferase] were transformed into yeast strain CY770 (described in U.S. Pat. No. 5,989,808; Ozenberger and Young, 1995) to generate interaction strain KY183. Plasmids pGBT9, KChIP1-pACT2 and Kp132 were transformed into yeast strain CY770 to generate control strain KY186. Plasmids hKv4.3N-pGBT9, pACT2 and Kp132 were co-transformed into yeast strain CY770 to generate control strain KY185. Plasmids pGBT9, pACT2, and Kp132 were co-transformed into yeast strain CY770 to generate control strain KY188. Luciferase assays were performed as described previously. Initial testing of the low copy number plasmid demonstrates that the absolute luciferase signal was approximately one third of that generated using a 2-micron version of the luciferase reporter when tested in a similar hKv4.3 and KChIP1 two-hybrid interaction. However, the CEN version of the luciferase reporter still provides a 100-fold increase in luciferase activity of test strain in comparison to negative control strain (see FIG. 5; left side).

Two interacting proteins expressed as fusions to the Gal4 DNA binding domain (BD) and the Gal4 activation domain (AD) interacted and drive expression of a GAL-reporter gene, in this case luciferase. The Kv4.3 protein and KChIP1 protein were expressed as fusion proteins in this system with the Gal1/10-luciferase reporter gene. Luciferase activity showed a 30-fold increase in the strain that contained both fusion proteins, in comparison to a yeast strain that contained only one fusion protein and an empty vector.

EXAMPLE 6

Yeast Two-hybrid System that Employs the Luciferase Gene as a Reporter Gene (G-alphaZ and RGSZ Interaction)

To demonstrate the functionality of the luciferase reporter gene in yeast, a yeast two-hybrid experiments was performed to test whether G-alphaZ (GaZ) interacts with RGS-Z. Molecular cloning techniques were carried out using standard methods (Curr Prot. In Mol. Biol). Restriction digests were performed as to manufacturer's specifications. Where appropriate to the cloning scheme, cDNA fragments were end-filled to generate blunt ends using Klenow, and standard techniques. Dephosphorylation of cDNA fragments and/or vectors was conducted using Shrimp Alkaline Phosphotase (SAP) according to manufacturer's instructions (Boehringer Manheim or Amersham Life Science). Ligation reactions were conducted using standard techniques, and recombinant vectors were transformed into $E.\ Coli$ DH5α cells (Gibco, LTI) and plated on LB-agar plates containing appropriate antibiotic(s). Colonies were recovered and plasmid DNA prepared using either DNA midi prep kits, or automated DNA preparation (Qiagen). The integrity of plasmids and cloning strategies were confirmed using reagents from Perkin-Elmer, and automated sequencing equipment from ABI.

The complete ORFs for G-alphaZ and RGS-Z were isolated from a human brain cDNA library (Quickclone cDNA, Clontech) by PCR amplification. PCR primers were designed 5' and 3' of the open reading frame of G-alphaZ (GenBank #J03260) and RGS-Z (Genbank #AF074979). PCR amplification was performed under standard buffer conditions using the Clontech cDNA Advantage cDNA kit. The primers were G-alphaZ-fwd 5' ACCATGGGATGTCGGCAAAGCTCAGAGGAAA-3' (SEQ ID NO: 17) and G-alphaZ-rev 5'-CAAGGGG-TGGGGGACATT-3' (SEQ ID NO: 18) for G-alphaZ and RGS-Z-fwd 5'-CCCGGCCGGCAGGTGGAC-3' (SEQ ID NO: 19) and RGS-Z-rev 5'-CTCATGCMAATAAA-AGTGGTTC-3' (SEQ ID NO: 20) for RGS-Z. Cycle parameters were 94° C. for 30 seconds, 55° C. for 30 seconds and 72° C. for 1 minute for a total of 30 cycles.

Amplified DNA fragments corresponding to the expected product lengths of 1191 bp and 1035 bp for G-alphaZ and RGS-Z respectively, were gel purified using GeneClean Spin columns (Bio101). The gel purified fragments were then TA-subcloned in the pCRII-TOPO vector (Invitrogen). Inserts of several individual clones were confirmed by fluorescent dye terminating sequencing on an ABI automated DNA sequencer.

The pCRII plasmid containing the entire ORF of G-alphaZ was digested with NcoI and EcoRI. The insert containing the G-alphaZ ORF was gel purified and ligated directionally in frame in the NcoI and EcoRI sites of the vectors pGBKT7 (Clontech) and pACT2 (Clontech) to generate GaZ-pGBKT7 and GaZ-pACT2, respectively. The pCRII plasmid containing the entire wild-type ORF of RGS-Z was digested with XhoI and BamHI, blunt-ended, and after gel-purification, the insert was ligated in frame in the SmaI site of pGBKT7 and pACT2 to generate RGSZ-pGBKT7 and RGSZ-pACT2, respectively.

A constitutively active (Q205L; Wang et al., 1998) form of G-alphaZ was generated. The Q205L mutation in G-alphaZ was generated in the GaZ-pGBKT7 and GaZ-pACT2 plasmids using the QuickChange kit (Stratagene) and the primers 5'-GTGGGGGGGCTGAGGTCAGAG-3' (SEQ ID NO: 21) and 5'-CTCTGACCTCA-GCCCCCCCAC-3' (SEQ ID NO: 22). Recombinant mutant plasmids were transformed into bacterial cells and DNA isolated using standard methods. The Q205L G-alphaZ mutants were identified by sequence analysis of the resulting colonies and termed Q205LIGaZ-pGBKT7 and Q205UGaZ-pACT2.

Yeast strains were transformed using a lithium acetate procedure and plated on appropriate media (Rose et al., 1990). All yeast media and reagents were prepared using standard methods. Yeast transformants for appropriate test and control strains were grown for 3–4 days at 30° C. on plasmid retention media. The activation and binding domain vectors containing Q205L/GaZ and RGS-Z were transformed into yeast strain CY770 (Ozenberger and Young, 1995) together with a ura-marked plasmid containing either the cycloheximide (CYH2) reporter (pOZ146; U.S. Pat. No. 5,989,808; Young et al., 1998) or the luciferase reporter (Kp126). The generated yeast strains and designations are summarized in Table 2.

To test the ability of Q205L/GaZ and RGS-Z to interact in a two-hybrid system and drive expression of the downstream reporter genes, the histidine reporter activity was tested. Representative colonies of each strain were isolated and resuspended in 100 μl water. Aliquots of 5 μl the resuspended colonies were then aliquoted on agar plates containing plasmid retention media also lacking histidine and containing increasing concentrations 3-amino triazole (Sigma) to test the histidine reporter. Yeast strains that contain both Q205L/GaZ and RGS-Z fusion proteins demonstrated histidine prototrophy and growth on selective media in comparison to control strains.

The two-hybrid interaction strains co-expressing Q205L/GaZ and RGS-Z fusion proteins in CY770 in combination with the cycloheximide (CYH2) reporter were tested. The majority of the colonies from the interacting strain (ybn66) failed to grow on increasing concentrations of cycloheximide, indicating a positive interaction between Q205L/GaZ and RGS-Z. The negative control colonies expressing Q205L/GaZ, or RGS-Z with an empty vector continue to grow on cycloheximide (See FIG. 6A).

Figure 6B:
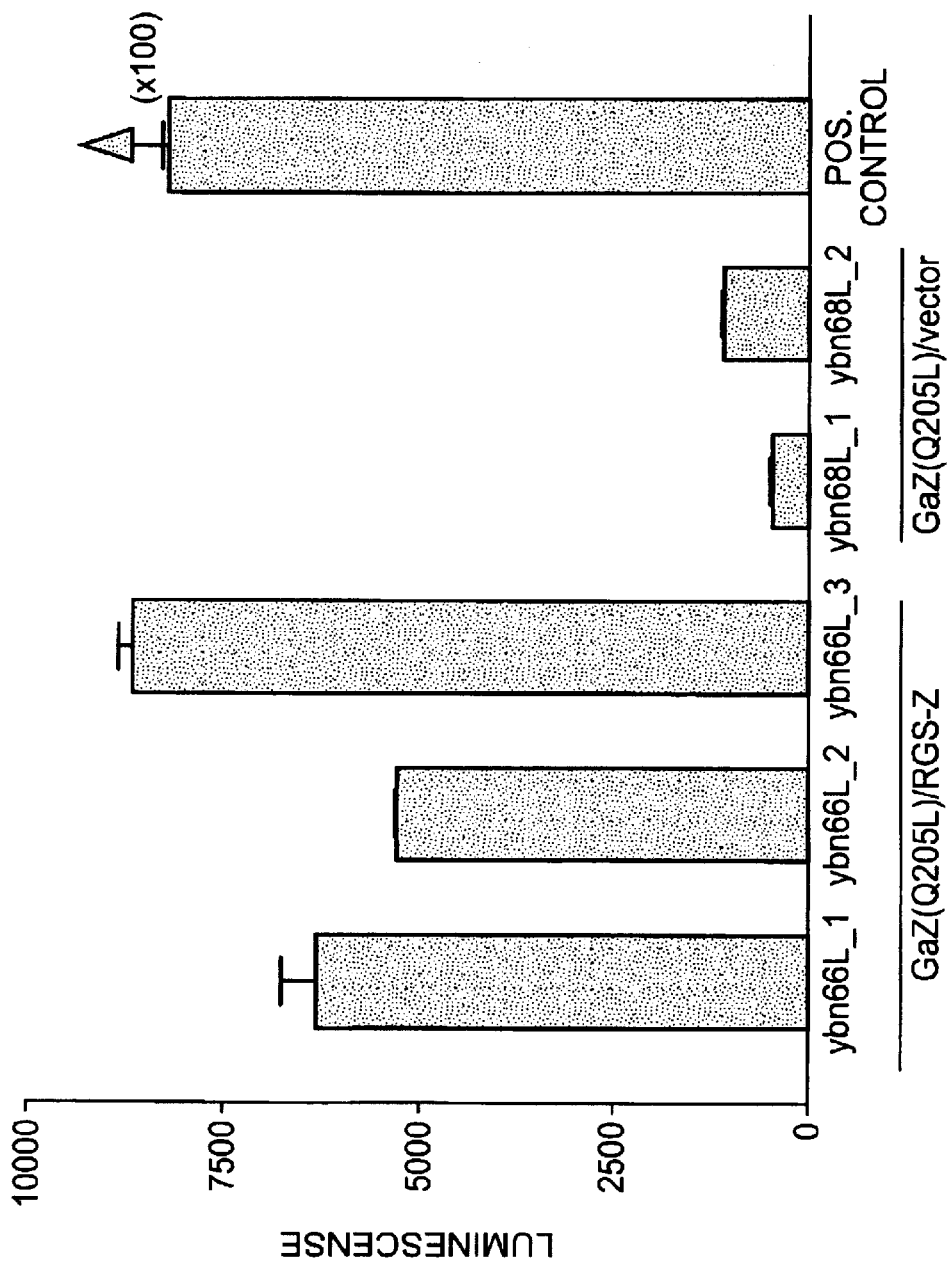
FIG. 6B is a graph representing the luciferase activity found in the ybn66L strain (Table 2), shown in three separate trials, as compared to a negative control (strain ybn68L) and a positive control.

The interaction between Q205/GaZ-pGBKT7 and RGS-Z-pACT2 was also tested for activation of the luciferase reporter in a two-hybrid system. To test the ability of the interaction of this protein pair (Q205L/GaZ-BD and RGS-Z-AD) to drive expression of the downstream reporter gene, a luciferase assay was performed as described previously. Briefly, colonies were inoculated in 3 mls plasmid retention (SC-leucine, -tryptophan-uracil) yeast medium and grown overnight at 30° C. Cell density was measured at $OD_{600}$ and densities were adjusted to an $OD_{600}$ of 0.2. Cells were seeded in 96-well plates (100 ul) and grown for an additional 2–3 hrs. Luciferase substrate was added (100 ul), and the plate was incubated for 50 minutes, in the dark at room temperature, while shaking. Luciferase activity was determined using a 2 second read on a TopCount luminometer (Packard),. As shown in FIG. 6B, there was a five to ten-fold induction of luciferase activity in the interaction strain when compared to the controls strains. Differences in the level of luciferase detected between the individual colonies were attributed to slight variability in the 2 micron plasmid copy number or by individual colony growth rates.

EXAMPLE 7

Yeast Two-hybrid (YTH) Single Point Screening

Cultures were grown overnight for independent comparative strains (RGS, and 4.3) in 250 ml tissue culture flasks containing with 50 ml SC-ura-leu-trp medium inoculated with approximately 100 ul of a saturated culture [<1 month, kept at 4° C.]. Following the overnight incubation, the cell

TABLE 2

| Strain | BD Vector trp | AD Vector leu | Reporter ura | yeast background |
|---|---|---|---|---|
| ybn66 | GaZ_Q205L_pGBKT7 | RGS-Z_pACT2 | cyh2 | CY770 |
| ybn66L | GaZ_Q205L_pGBKT7 | RGS-Z_pACT2 | luc | CY770 |
| ybn67 | RGS-Z_pGBKT7 | GaZ_Q205L_pACT2 | cyh2 | CY770 |
| ybn67L | RGS-Z_pGBKT7 | GaZ_Q205L_pACT2 | luc | CY770 |
| ybn68 | pGBKT7 | RGS-Z_pACT2 | cyh2 | CY770 |
| ybn68L | pGBKT7 | RGS-Z_pACT2 | luc | CY770 |
| ybn69 | RGS-Z_pGBKT7 | pACT2 | cyh2 | CY770 |
| ybn69L | RGS-Z_pGBKT7 | pACT2 | luc | CY770 | density was determined at $OD_{600}$, and was between.0.15 and 0.6. The culture was diluted as necessary to a final density of $OD_{600}$=0.15 with SC-ura-leu-trp medium. A 96-well plate was seeded with 100 µl cells/well. Compounds were introduced into the wells using a 96-well replicator to inoculate the wells with approximately 1 µl compound. Plates were sealed and incubated at 30° C. for 2 hours. After 2 hours, the plates were unsealed and 100 µl LucLite (Packard) luciferase substrate was added to each well. Plates were resealed and incubated at room temperature on a shaker for 50 minutes in the dark. Plates were counted on a Packard TopCount plate counter for 2 seconds per well after 1 minute dark equilibration (inside machine).

Total counts per assay/well were divided by the total counts for DMSO (3%) control wells to provide the percentage inhibition for each compound per strain compared to negative control strain. Different strains served as a control for each specific test strain.

Compounds that showed an inhibition in the single point assays were tested in the dose response curves as described above. Compounds were evaluated in the test and control strains. FIG. 7A shows that compound SBQ-1B3 demonstrates specific modulation of the luciferase activity in the hKv4.3N / (1 v) KChIP1 interaction yeast strain versus the Q205L/GaZ and RGS containing yeast strain. In contrast, compound SBQ-3D10 (FIG. 7B) has a specific effect (decrease) on luciferase activity in the hKv4.3N/KChIP1 interaction in comparison to the Q205L/GaZ and RGS containing yeast strain.

These experiments demonstrate that the luciferase reporter as employed in yeast two-hybrid experiments has utility in the identification of modulators, in this case small molecules. However, this assay format would be of general utility in the evaluation of other modulating entities such as peptides, antibodies, linked chemicals, or other polypeptides that would be potential modulators of any protein-protein interaction of interest.

EXAMPLE 8

A Yeast Two-hybrid System that Employs the Luciferase Gene as a Reporter Gene (Anti-KChIP1 Single Chain Antibody [ScFv_E2] and hKChIP1 (Epitope) Interaction)

Molecular reagents for ScFV (anti KChIP1) were generated using the following methods. mRNA was isolated from hybridoma cell lysate (K55/82) and CDNA was prepared by standard methods. Variable light and heavy chain sequences were PCR amplified and assembled using the Recombinant Phage Antibody System (Amersham/Pharmacia). Assembled single chain antibody PCR products were then TA-cloned in pCRII vector (In vitrogen) and sequence analyzed. Due to some recombination event, direct subcloning of the inserts into the yeast two-hybrid vectors pAS and pACT2, was problematic; therefore the inserts were instead PCR amplified using M13 forward and reverse primers using the pCRII single chain recombinants as template. PCR products of in approximately 1 kb (ScFv coding region plus portions of the MCS) were gel-purified and restriction digested with NcoI and EcoRV. The 900 bp NcoI-EcoRV fragments were gel-purified and ligated into the pAS and pACT2 vectors cut with NcoI and SmaI to generated ScFV_E2-pAS and SCFv_E2-pACT2, respectively. Due to the instability of the single chain antibody DNA, the ligated products were transformed in competent STBL2 cells (Life Technologies) and plated on appropriate media and were incubated at 30° C. A number of colonies were selected for recombinant DNA preparation and plasmid sequence was confirmed by DNA sequence analysis.

To generate yeast strains expressing ScFv_E2 and hKChIP1, recombinant yeast two-hybrid plasmids that express the single chain antibody (ScFv_E2-pAS and ScFv_E2-pACT2) were co-transformed with the recombinant yeast two-hybrid plasmids which express the epitope hKChIP1 [hKChIP1-pAS and hKChIP1-pACT2] and Kp126 (Gal-luc) into the parent yeast strain CY770. Notably, any transformation that had included the recombinant ScFc_E2-pACT2 plasmid resulted in no yeast colonies, and therefore this particular recombinant was likely lethal. The appropriate test and control strains were generated and are summarized in Table 3 below.

TABLE 3

| Strain | BD Vector trp | AD Vector leu | Reporter ura | Yeast background |
| --- | --- | --- | --- | --- |
| ybn11L | ScFv_E2-pAS | HKChIP1-pACT2 | luc | CY770 |
| ybn12L | KChIP1-pAS | ScFv_E2-pAS | luc | CY770 |
| ybn13L | ScFv_E2-pAS | pACT2 | luc | CY770 |
| ybn14L | pAS | ScFv_E2-pACT2 | luc | CY770 |
| ybn15L | pAS | hKChIP1-pACT2 | luc | CY770 |
| ybn16L | HKChIP1-pAS | pACT2 | luc | CY770 |

Figure 8:
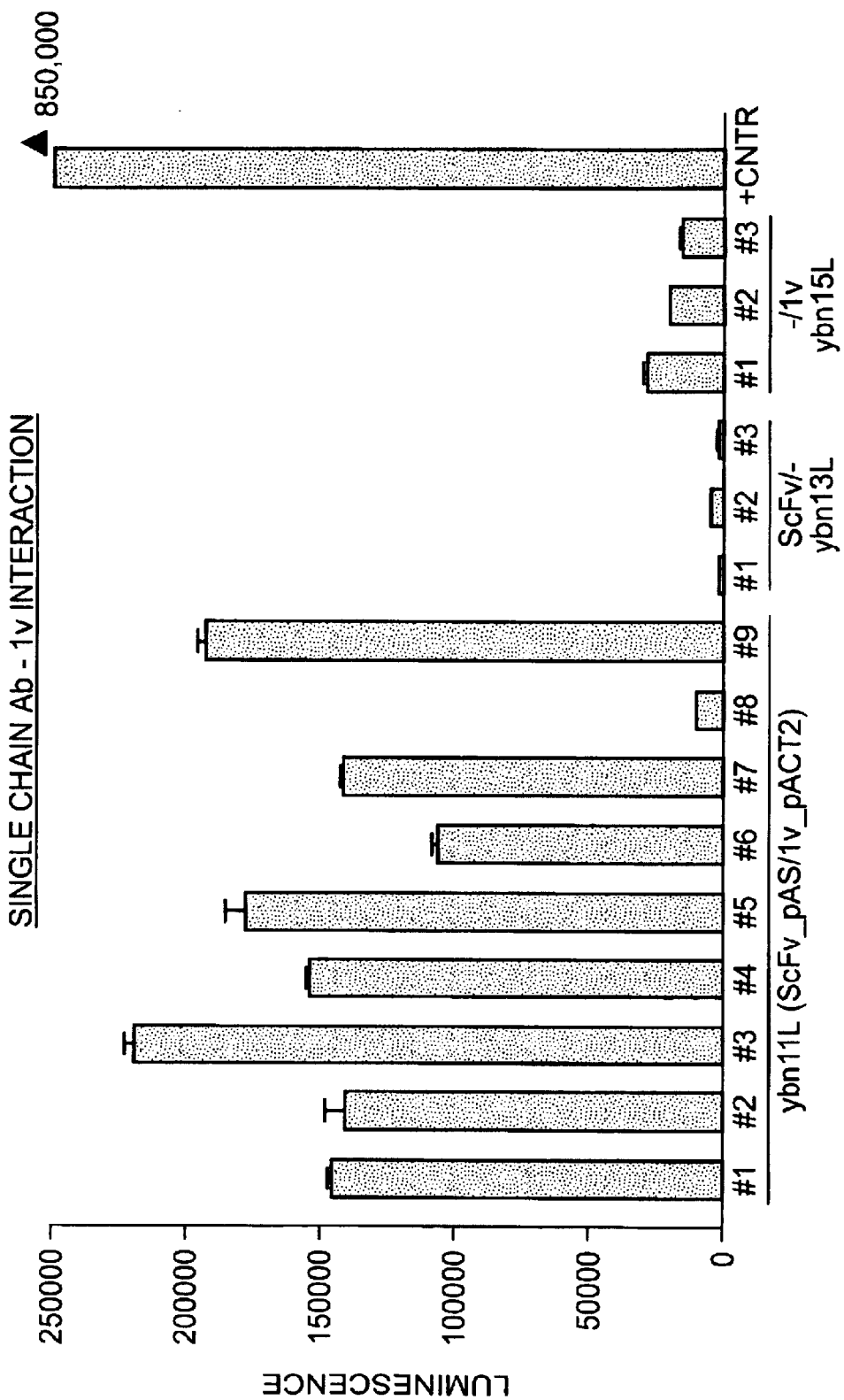
FIG. 8 is a graph depicting the luciferase activity present in yeast strain ybn11L, which expresses both the ScFv_E2-pAS and hKChIP1-pACT2 to yield a productive protein-protein interaction. Negative control strains ybn13L and ybn15L are also presented.
Figure 9:
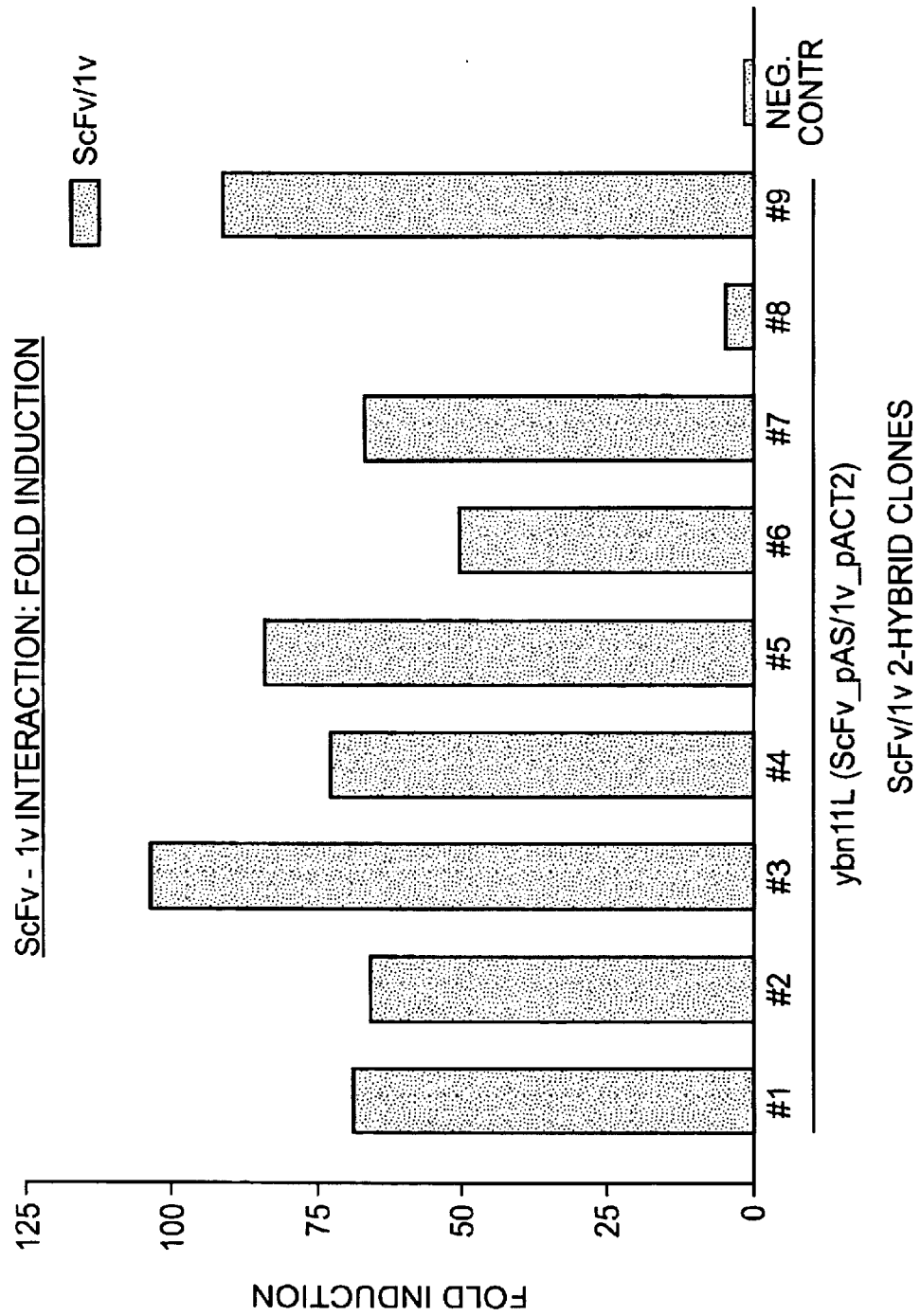
FIG. 9 is a graph depicting the fold activation of the luciferase reporter gene in yeast strain ybn11L, which expresses both the ScFv_E2-pAS and hKChIP1-pACT2 to yield a productive protein-protein interaction.

Appropriate test and control strains were tested for yeast two-hybrid driven luciferase reporter gene activity, as previously described. The yeast strain [ybn11L] which expresses both the single chain antibody ScFv_E2-pAS with the hKChIP1-pACT2 resulted in a productive protein-protein interaction and drives expression of the downstream luciferase reporter gene when compared to control strains that express either the ScFv_E2-pAS fusion protein [ybn13L] or the hKChIP1-pACT2 fusion protein [ybn15L] with a companion empty vector (see FIG. 8). As shown in FIG. 9, the interaction-positive yeast strain ybn11L, which contains both the single chain antibody and epitope fusion proteins, resulted in a 75-fold increase in luciferase activity. In addition, the interaction of the ScFv_E2-pAS and hKChIP1-pACT2 fusion protein also drives expression of a downstream CYH2 gene, and resulted in sensitivity to cycloheximide and lack of cell growth on selective media in comparison to control strains.

EXAMPLE 9

Generation of Strains Using the pEKI-Ren Reporter Gene

To assess the utility of *Renilla reniformis* luciferase as a reporter gene, the *Renilla reniformis* luciferase coding region plus SV40 polyadenylation signal was obtained by an NheI and BamHI double-digestion of pRL-null vector (Promega; Genbank accesion #AF025844). The 1197 base-pair fragment was blunt-ended and ligated to pEK-1 vector previously digested by BamHI and blunt-ended to generated plasmid pEK1-Ren. Recombinant plasmid was transformed into bacterial cells, purified, and confirmed by sequence analysis.

Yeast strains analogous to those generated for two-hybrid interactions with the Kp126 (firefly luciferase) were generated using the Renilla luciferase reporter. Yeast strain CY770 was co-transformed with plasmids encoding two-hybrid fusion for G-alphaZ(Q205L), RGS-Z and the reporter pEK1-Ren to generated test and control strains. Similarly, CY770 was co-transformed with hKv4.3-pGBKT7 and KChIP1-pACT2 and the reporter plasmid pEK1-Ren to generate test and control strains as summarized in Table 4.

TABLE 4

| Strain | BD Vector trp | AD Vector leu | Reporter ura | yeast background |
|---|---|---|---|---|
| ybn70L | Q205L/GaZ-pGBKT7 | RGSz-pACT2 | RenLuc | CY770 |
| ybn71L | Q205L/GaZ-pGBKT7 | pACT2 | RenLuc | CY770 |
| ybn72L | pGBKT7 | RGSz-pACT2 | RenLuc | CY770 |
| ybn73L | pGBKT7 | pACT2 | RenLuc | CY770 |
| ybn77L | hKv4.3N-pGBT9 | KChIP1-pACT2 | RenLuc | CY770 |
| ybn78L | hKv4.3N-pGBT9 | pACT2 | RenLuc | CY770 |
| ybn79L | pGBT9 | KChIP1-pACT2 | RenLuc | CY770 |

Strains were subsequently investigated for a productive two-hybrid interaction to drive expression of the *Renilla reniformis* luciferase reporter gene. Briefly, colonies were inoculated in 3 ml of plasmid retention media (SC-leu-trp-ura) and grown overnight at 30° C. Cell density was measured at $OD_{600}$ and adjusted to an appropriate cell density (0.1 to 0.5 OD). Yeast cells were seeded in 96 wells in 100 µl aliquots and grown for an additional 2–hours at 30° C. Renilla luciferase substrate (Promega) was added to the plate and luminescence determined in the appropriate time period (1–10 min; as per manufacturer's instructions). Renilla luciferase activity was determined using a 2 second read on a Top Count luminometer (Packard). Assays were conducted in triplicate and values averaged.

To assess the utility of the Renilla luciferase as a reporter gene for yeast two-hybrid interactions, the interaction between hKv4.3N and KChIP1, as well as the interaction between RGSz and Q205L/GaZ, were evaluated. Appropriate test and control strains were tested as previously described. For the RGSz and Q205L/GaZ interaction, the yeast strain [ybn70L) which expressed both the Q205L/GaZ-pGBKT7 and RGSz-pACT2 fusion proteins resulted in a productive protein-protein interaction to drive expression of the downstream Renilla luciferase reporter gene. In contrast, control strains that express either the Q205L GalphaZ-pAS fusion protein [ybn71L] or the RGSz-pACT2 fusion protein [ybn72L] with an empty companion vector did not reveal any luciferase activity. The strain ybn73L that contains both empty vectors (pAS and pACT2) did not exhibit Renilla luciferase gene expression. The interaction yeast strain ybn70L, which contains both fusion proteins results in a 40-fold increase in Renilla luciferase activity.

Similar results were observed for hKv4.3N and hKChIP1 interaction. The yeast strain ybn77L that expresses both fusion proteins (from hKv4.3N-pGBT9 and KChIP1-pACT2] resulted in a productive protein-protein interaction able to drive expression of the Renilla luciferase reporter gene. Luciferase activity was much higher in comparison to control yeast strains, ybn78L and yBN79L, which contain a single fusion protein, h4.3N-pGBT9 or KChIP1-pACT2 respectively, and the companion empty vector. The productive interaction between the hKv4.3N and hKChIP1 fusion proteins resulted in a 25-fold increase in Renilla luciferase activity in a two-hybrid system.

EXAMPLE 10

Multiplex Assays Using Strains Expressing Different Luciferase Reporter Genes (Firefly Luc Reporters and Renilla Luc Reporter)

Demonstration of *Renilla reniformis* reporter gene activity in the two different yeast two-hybrid interaction strains (RGSz & Galphaz Q205L; and hKv4.3 & KChIP1), enables effective multiplexing of the strains for various screen applications. Use of independent reporter genes enables mixing of yeast strains within one assay sample or well (multiplexing). In addition, use of independent reporter genes enables immediate assessment and identification of the responding strain. Previously, multiplexing of several samples wherein all strains used the same reporter gene required extensive follow-up deconvolution to determine which specific strain may have accounted for the reporter gene activity. Use of two different reporter genes provides several advantages: 1) economy of assays (condenses two separate assays into a single well, decreases the amount of supplies, and use of limited compound resources); 2) increased integrity of assays for controls, since compound application and evaluation in one well decreases interwell variability, for example, variability by pipetting etc.; and 3) increased ability to tailor control of assay conditions to the dynamics of the two-hybrid interaction to a particular protein-protein interaction.

Figure 10:
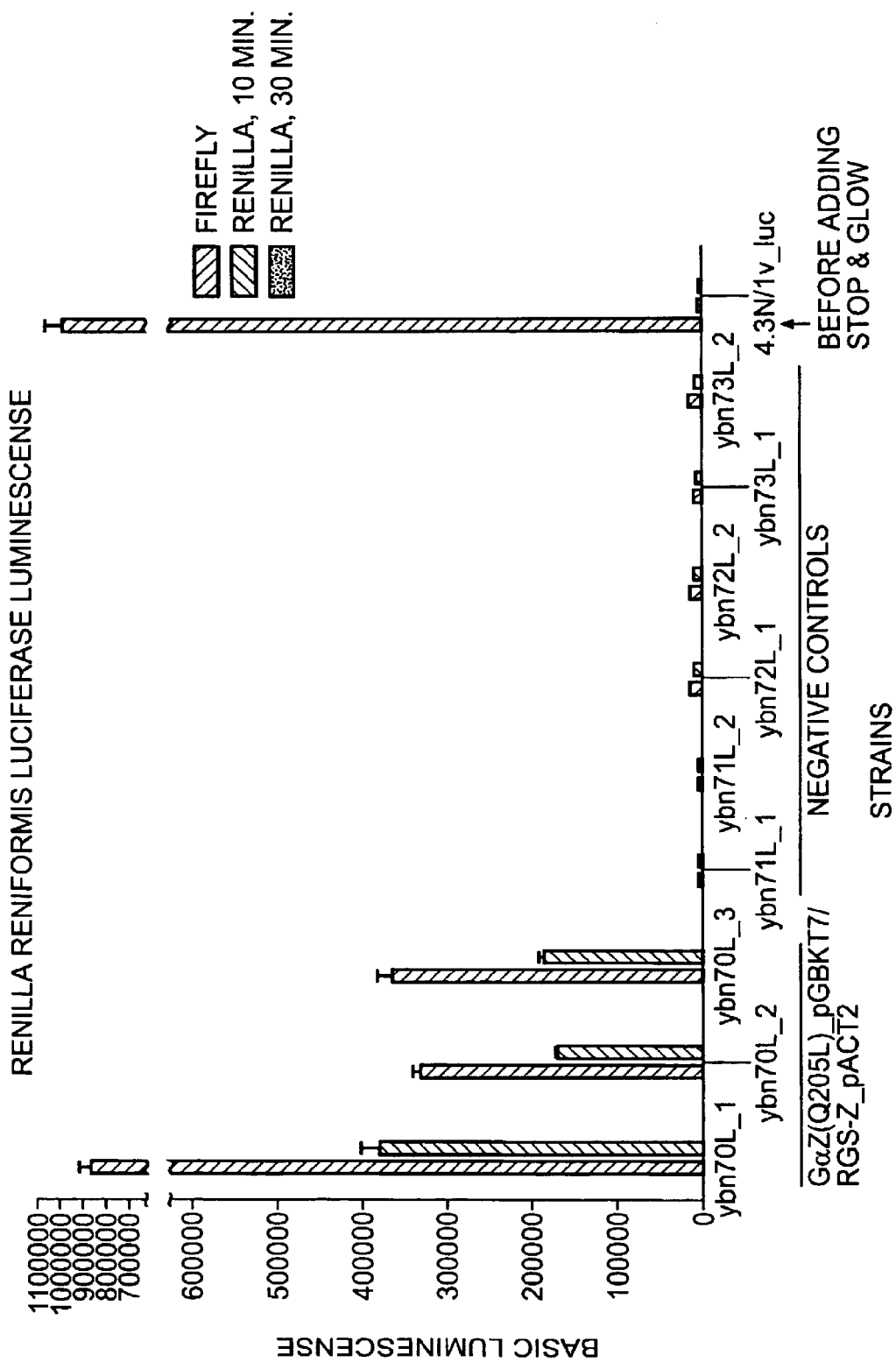
FIG. 10 is a graph demonstrating the level of *Renilla reniformis* luciferase and *Photinus pyralis* (firefly) luciferase activities in mixed yeast cell cutures. Renilla luciferase activity resultied from the protein-protein interaction of Q205L/GaZ and RGS-Z.
Figure 11:
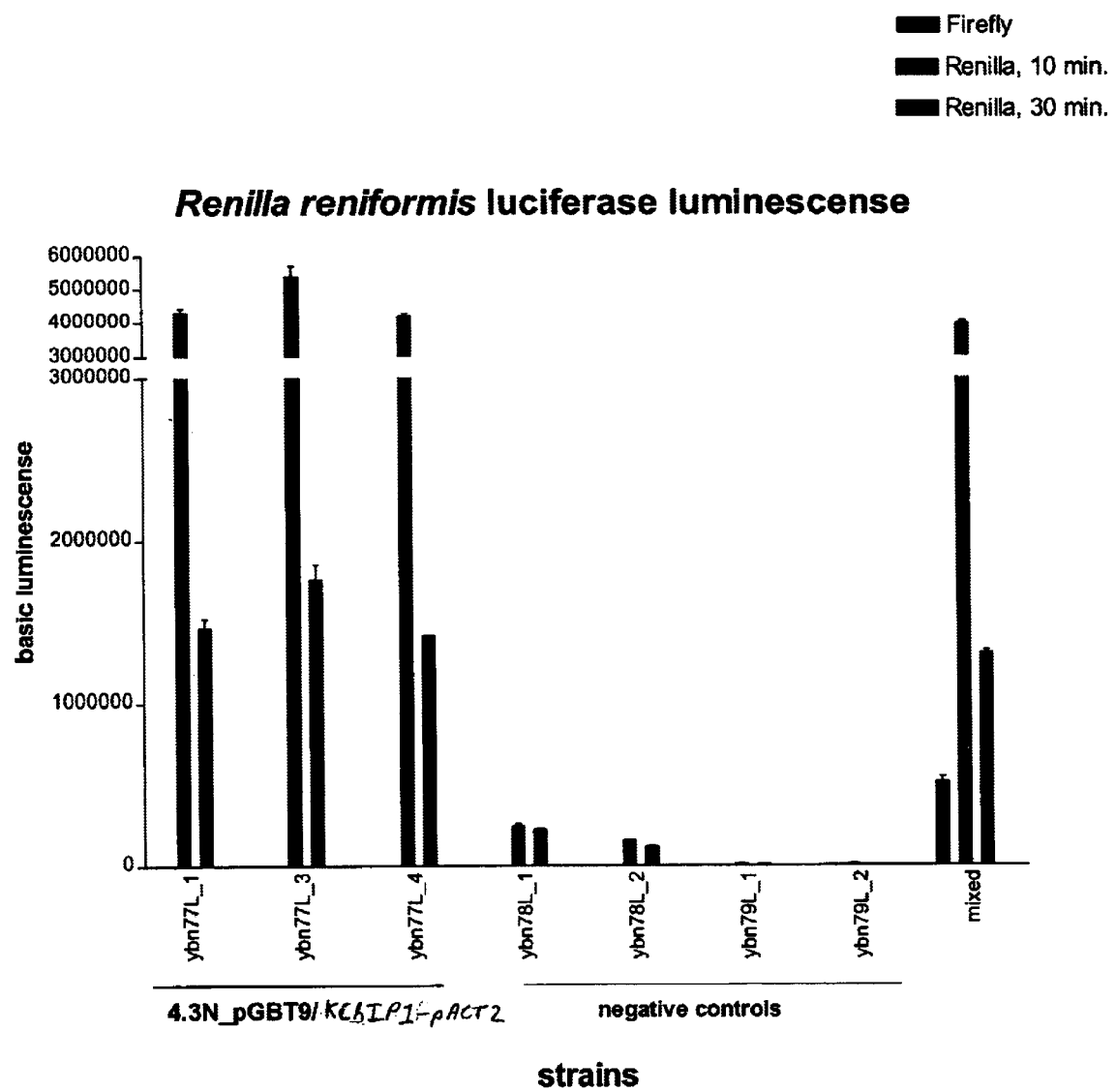
FIG. 11 is a graph demonstrating the level of *Renilla reniformis* luciferase and firefly luciferase activities in mixed yeast cell cutures. Renilla luciferase activity resulted from the protein-protein interaction of 4.3N_pGBT9 and KChIP1_pACT2.

To demonstrate the ability to mix two independent two-hybrid yeast strains, each using a separate luciferase reporter gene, into one assay well (that is, multiplex), the yeast strain expressing Q205L/GaZ and RGS-Z as fusion proteins and containing the firefly luciferase reporter gene (ybn66L) and the yeast strain expressing the hKv4.3 and KChIP1 fusion proteins and containing the Renilla luciferase reporter gene (ybn77L) were tested. Yeast strains were grown overnight in plasmid retention media at 30° C., and cell density determined at $OD_{600}$. Various percentages of each strain were mixed and assays were performed for both forms of luciferase activity. The two strains were mixed in the ratios (µl) 100:0, 75:25, 50:50, 25:75, and 0:100 for ybn66L (Q205L/GaZ and RGS-Z) and ybn77L (hKV4.3 and KChIP1), respectively. Strains were tested at equal cell densities (OD 0.15) or at different cell densities (OD=0.25 for ybn66L and OD=0.15 for ybn77L). Yeast cells for each two-hybrid strain were mixed appropriately, and tested for two-hybrid driven luciferase activity following the general luciferase assay as described previously. Yeast cells were seeded into a 96 well plate, and incubated for approximately 3 hours at 30° C. Firefly luciferase substrate (Promega or Packard) was added and cells were incubated for approximately 30 minutes, shaken at room temperature in the dark. Firefly luciferase activity was determined using a 2 second read on a TopCount luminometer (Packard). Substrate for Renilla luciferase was then added to the same well(s) and Renilla luciferase activity was determined using a 10 second read on a TopCount luminometer (Packard). The fold increases in luciferase activities for each yeast strain and with the individual luciferase reporter gene were similar to that observed when tested individually, as a single strain per assay well. In the multiplexing of these two strains, all combinations enabled detection of two-hybrid driven luciferase activity. The most suitable ratio appeared to be the 75:25 ratio of strains having cell densities OD =0.25 and 0.15 for ybn66L and ybn77L; respectively. This combination resulted in firefly luciferase activity of approximately 950,000 luminescence units, and Renilla luciferase activity of approximately 4,500,000 luminescence units; and clearly discernable from control strains (see FIGS. 10 and 11).

The multiplexed format is used to evaluate the effects of modulators (small molecules, expressed peptides, or other molecules) of the protein-protein interaction of interest. For example, cells from independent two-hybrid yeast strains are mixed in the appropriate ratio and aliquoted into a 96 well plate. Compounds are added and cells incubated as described previously. Luciferase activity is determined for each reporter gene as described previously. The luciferase activity of each strain is normalized to a compound negative (vehicle control) well. Effect of compound is noted by a change in luciferase activity. A specific effect of a compound on one protein-protein interaction is noted by a change in luciferase activity on only one of the test strains. For example, a compound with potential specific effects on hKv4.3 and KChIP1 interaction would affect luciferase activity in yeast strain ybn77L, while no effect on luciferase activity would be observed in ybn66L that contains Q205L/GaZ and RGS-Z. In addition, a compound that blocks the protein-protein interaction would be observed as a decrease in luciferase activity.

The publications and patents cited herein are incorporated by reference in their entirety.

Aflalo C. (1990). Targeting of cloned firefly luciferase to yeast mitochondria. Biochem. 29:4758–4766.

An et al., (2000) Modulation of A-type potassium channels by a family of calcium sensors. Nature 403(3):553–556.

Baumbach W R, Horner D. and J S Logan. (1989) The growth hormone-binding protein in rat serum is an alternatively spliced form of the rat growth hormone receptor. Genes & Devel. 3:1199–1205.

Boylan M, Leeetier J, and Meighen E A. (1989) Fused bacterial luciferase subunits catalyze light emissions in eukaryotes and prokaryotes. J. Biol. Chem. 264:1915–1918.

Butt T R, Sternberg E J, Gorman J A, Clark P. Hamer D, Rosenberg M and S T Crooke. (1984) Copper metallothionein of yeast, structure of the gene and regulation of expression. Proc. Natn. Acad. Sci. USA 81:3332–3336.

Chein, C-T., Bartel, P L., Sternglanz R. and S. Fields (1991) The two-hybrid system: A method to identify and clone genes for proteins that interact with a protein of interest. Proc. Natl. Acad. Sci., USA 88: 9578–9582.

Cunningham B C, Ultsch M, De Vos A M, Mulkerrin M G, Clauser K R and J A Wells. (1991) Dimerization of the extracellular domain of the human growth hormone receptor by a single hormone molecule. Science 254:821–825.

Davis J and D I H Linzer. (1989) Expression of multiple forms of the prolactin receptor in the mouse liver. Mol. Endocrinol. 3:674–680.

Davis S, Aldrich T H, Stahl N, Pan L, Taga T, Kishimoto T, Ip NY and G Yancopoulos. (1993) LIFR and gp 130 as heterodimerizing signal transducers of the tripartate CNTF receptor. Science 260:1805–1808.

De Wet J R, Wood K V, DeLuca M, Helinski D R, Subramani S. (1987) Firefly liciferase gene: Structure and Expression in mammalian cells. Mol. Cell. Biol. 7(2):725–737.

Durfee T., Becherer K., Chen P-L., Yeh, S-H., Yang Y., Kilburn A E., Lee W-H. and S J Elledge. (1993) The retinoblastoma protein associated with the protein phosphatase type 1 catalytic subunit. Genes and Devel. 7:555–569.

Elledge S J and R W Davis. (1988) A family of versatile centromeric vectors designed for use in the sectering-shuffle mutagenesis assay in *Saccharomyces cerevisiae.* Gene 70:303–312.

Fields S and O. Song. (1989) A novel genetic system to detect protein-protein interactions. Nature 340:245–246.

Finny M. (1992) The polymerase chain reaction. In: Current Protocols in Molecular Biology. Chapter 15 Eds (F M Ausubel, R Brent, R E Kingston, D D Moore, J G Seidman, J Smith and K Struhl) John Wiley & Sons, NY.

Fischer E, Mitchell R, Hartman T, Silva T. Gospodarowicz D, Fiddes J C, and J A Abraham. (1991) The human gene for vascular endothelial growth factor. Multiple protein forms are encoded through alternative exon splicing. J. Biol. Chem. 266:11947–11954.

Fuh G., Cunningham B C, Fukunaga R, Nagata S, Goeddel D V and J A Wells. (1992) Rational design of potent antagonists to the human growth hormone receptor. Science 256:1677–1680.

Fuh G, Colosi P, Wood W I and J A Wells. (1993) Mechanism-based design of prolactin receptor antagonists. J. Biol. Chem. 8:5376–5381.

Glick J L, Meigs T E, Miron A, Casey P J. (1998) RGSZ1, a Gz-selective regulator of G-protein signaling whose action is senstive to the phosphoylation state of Gz-alpha. J. Biol. Chem. 273: 26008–26013.

Hill J E, Myers A M, Koerner T J and A Tzagoloff. (1986) Yeast/*E.Coli* shuttle vectors with multiple unique restriction sites. Yeast 2:163–167.

Himes S R and Shannon M F. (2000) Assays for transcriptional activity based on the luciferase reporter gene. Methods in Mol. Biol. 130:165–174.

Kang Y-S, Kane J, Kurjan J, Stadel J M and D J Tipper. (1990) Effects of expression of mammalian G and hybrid mammalian-yeast G proteins on the yeast pheromone response signal transduction pathway. Mol. Cell. Biol. 10:2582–2590.

Kondo M, Takeshita T, Ishii N, Nakamura M, Watenabe S, Arai K-i and K Sugamura. (1993) Sharing of the interleukin-2 (IL-2) receptor chain between receptors for IL-2 and IL-4. Science 262: 1874–1877.

Leung D, Spencer S A, Cachianes G, Hammonds G, Collins C, Henzel W J, Barnard R, Waters M J and W I Wood. (1987) Growth hormone receptor and serum binding protein: purification, cloning and expression. Nature 330:537–543.

Li, J J and I. Herskowitz (1993) Isolation of ORC6, a component of the yeast origin recognition complex by a one-hybrid system. Science 262:1870–1874.

Maniatus T, Fritsch E F and J Sambrook. (1982) Molecular Cloning. Cold Spring Harbor Laboratory Press.

Mui A and A Miyajima (1994) Cytokine receptors and signal transduction. In: Progress in Growth Factor Research. pp 15–35. Pergamon Press. NY Naylor L H. (1999) Reporter gene technology: The future looks bright. Biochemical Pharm. 58:749–757.

Noguchi M, Nakamura Y, Russell S M, Zeigler S F, Tsang M, Cao and W J Leonard. (1993) Interleukin-2 receptor chain: A functional component of the interleukin-7 receptor. Science 262:1877–1880.

Picard D, Schena M and K R Yamamoto. (1990) An inducible expression vector for both fission and budding yeast. Gene 86:257–261.

Rose M D, Winston F, and P Hieter. (1990) Methods in yeast genetics. Cold Spring Harbor Laboratory Press.

Shuey D J, Betty A, Jones P G, Khawaja X, Cockett M I. (1997) RGS7 attenuates signal transduction through the Galpha q family of heterotrimeric G-proteins in mammalian cells. J. Neurochem. 70:1964–1972.

Silverman L, Campbell R, Broach J R. (1998) New assay system technologies for high-throughput screening. Curr. Opin. In Chemical Biology. 2:397–403.

Stables J, Scott S, Brown S, Roelant C, Burns D, Lee M G, Rees S. (1999) Development of a Dual glow-signal firefly and renilla luciferase assay reagent for the analysis of G-protein coupled receptor signaling. J. Recept. Signal Transduction Res. 19(1–4):395–410.

Staten N R, Byatt J C and G G Krivi. (1993) Ligand-specific dimerization of the extracellular domain of the bovine growth hormone receptor. J. Biol. Chem. 268:18467–18473.

Su T-Z and M R El-Geweley. (1988) A multisite-directed mutagenesis using T7 DNA polymerase: application for reconstructing a mammalian gene. Gene 69:81–89.

Taga T and T Kishimoto (1993) Cytokine receptors and signal transduction. FASEB J. 7:3387–3396.

Taga T, Hibi M, Matsuda T, Hirano T and T. Kishimoto. (1993) IL-6-induced homodimerization of gp130 and associated activation of a tyrosine kinase. Science 260:1808–1810.

Tatsumi H, Masuda T, Nakano E. (1988) Synthesis of enzymatically active firefly luciferase in yeast. Agric. Biol. Chem. 52:1123–1127.

Terman B I, Dougher-Vermanzen M, Carrion M E, Dimitrov D, Armellina D C, Gospodarowicz D and P. Bohlen (1992) Identification of the KDR tyrosine kinase as a receptor for vascular endothelial cell growth factor. Biochem. Biophys. Res. Comm. 187:1579–1586.

Terman B I, Carrion M E, Kovach E, Rasmussen B A, Eddy R L and Shaws B. (1991). Identification of a new endothelial cell growth factor receptor tyrosine kinase. Oncogene 6: 1677–1683.

Vieites J M, Navarro-Garcia F, Perez-Diaz, Pla J, and Nombela C. (1994) Expression and in vivo determination of firefly luciferase as gene reporter in *Saccharomyces cerevisiae*. Yeast 10:1321–1327.

Yang X, Hubbard J A, and M Carlson (1992) A protein kinase substrate identified by the two-hybrid system. Science 257:31

Young K H and F W Bazer (1989) Porcine endometrial prolactin receptors detected by homologous radioreceptor assay. Mol. and Cell. Endocrinol. 64:145–154.

Young P R (1992) Protein hormones and their receptors. Curr. Opin. Biotech. 3:408–421.

Wade-Harper J, Adami G R, Wei N, Keyomarsk K and S J Elledge. (1993) The p21 Cdk-interacting protein Cip1 is a potent inhibitor of G1 Cyclin-dependent kinases. Cell 75:805–816.

Wang J. Ducret A, Ti Y, Kozasa T. Aebersold R, Ross E. (1998) RGSz1, a Gz-selective RGS protein in brain. J. Bio. Chem. 273:26014–26025.

Wilson T E, Fahrner T J, Johnston M and J Milbrandt. (1991) Identification of the DNA binding site for NGFI-B by genetic selection in yeast. Science 252:1296–1300.

We claim:

1. A yeast cell comprising:
   a) a nucleotide sequence encoding a first heterologous fusion protein comprising a first peptide of a known peptide binding pair that bind through extracellular interaction in their natural environment, or a segment thereof, joined to a transcriptional activation protein DNA binding domain;
   b) a nucleotide sequence encoding a second heterologous fusion protein comprising a second peptide of the binding pair, or a segment thereof, joined to a transcriptional activation protein transcriptional activation domain;
      wherein binding of the first peptide or segment thereof and the second peptide or segment thereof reconstitutes a transcriptional activation protein; and
   c) a luciferase gene activated under positive transcriptional control of the reconstituted transcriptional activation protein.

2. The yeast cell of claim 1 further comprising at least one endogenous nucleotide sequence selected from the group consisting of a nucleotide sequence encoding the transcriptional activation protein DNA binding domain, and a nucleotide sequence encoding the transcriptional activation protein transcriptional activation domain wherein at least one of the endogenous nucleotide sequences is inactivated by mutation or deletion.

3. The yeast cell of claim 1 wherein the peptide binding pair comprises a ligand and a receptor to which the ligand binds.

4. The yeast cell of claim 1 wherein the transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

5. The yeast cell of claim 1 wherein at least one of the heterologous fusion proteins is expressed from an autonomously-replicating plasmid.

6. The yeast cell of claim 5 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

7. The yeast cell of claim 6 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and transforming growth factor β ("TGF").

8. The yeast cell of claim 1 wherein the DNA binding domain is a heterologous transcriptional activation protein DNA binding domain.

9. The yeast cell of claim 8 wherein the DNA binding protein is selected from the group consisting of a mammalian steroid receptor and bacterial LexA protein.

10. The yeast cell of claim 1 wherein the yeast cell is Saccharomyces cerevisiae, Schizosaccharomyces pombe, or Pichia pastoris.

11. The yeast cell of claim 10 wherein the yeast cell is Saccharomyces cerevisiae.

12. The yeast cell of claim 1 wherein the luciferase gene is a Renilla luciferase gene.

13. The yeast cell of claim 1 wherein the luciferase gene is a Photinus luciferase gene.

14. The yeast cell of claim 1 wherein the first and second peptides of the peptide binding pair interact through extracellular interaction in their natural environment.

15. A yeast cell comprising:
   a) a nucleotide sequence encoding a first heterologous fusion protein comprising a first peptide of a peptide binding pair, or a segment thereof, joined to a transcriptional activation protein DNA binding domain;
   b) a nucleotide sequence encoding a second heterologous fusion protein comprising a second peptide of the peptide binding pair, or a segment thereof, joined to a transcriptional activation protein transcriptional activation domain;
      wherein the nucleotide sequence encoding either the first or second heterologous fusion protein is present in an effective copy number of at least 5 copies per yeast cell and the nucleotide sequence encoding the other heterologous fusion protein is present at a copy number of 1 or 2 per yeast cell; and
      wherein binding of the first peptide or segment thereof and the second peptide or segment thereof reconstitutes a transcriptional activation protein; and
   c) a luciferase gene activated under positive transcriptional control of the reconstituted transcriptional activation protein.

16. The yeast cell of claim 15 further comprising at least one endogenous nucleotide sequence selected from the group consisting of a nucleotide sequence encoding the transcriptional activation protein DNA binding domain and a nucleotide sequence encoding the transcriptional activation protein transcriptional activation domain, wherein at least one of the endogenous nucleotide sequences is inactivated by mutation or deletion.

17. The yeast cell of claim 15 wherein the peptide binding pair comprises a ligand and a receptor for the ligand.

18. The yeast cell of claim 15 wherein the transcriptional activation protein is Gal4, Gcn4, Hap1, Adr1, Swi5, Ste12, Mcm1, Yap1, Ace1, Ppr1, Arg81, Lac9, Qa1 F, VP16, or a mammalian nuclear receptor.

19. The yeast cell of claim 15 wherein at least one of the heterologous fusion proteins is expressed from an autonomously-replicating plasmid.

20. The yeast cell of claim 19 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

21. The yeast cell of claim 20 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

22. The yeast cell of claim 15 wherein the DNA binding domain is a heterologous transcriptional activation protein DNA binding domain.

23. The yeast cell of claim 22 wherein the DNA binding protein is selected from the group consisting of a mammalian steroid receptor and bacterial LexA protein.

24. The yeast cell of claim 15 wherein the yeast cell is *Saccharomyces cerevisiae, Schizosaccharomyces pombe,* or *Pichia pastoris.*

25. The yeast cell of claim 24 wherein the yeast cell is *Saccharomyces cerevisiae.*

26. The yeast cell of claim 15 wherein the luciferase gene is a Renilla luciferase gene.

27. The yeast cell of claim 15 wherein the luciferase gene is a Photinus luciferase gene.

28. The yeast cell of claim 15 wherein the first and second peptides of the peptide binding pair interact through extracellular interaction in their natural environment.

29. A method of detecting the interaction of a first peptide and a second peptide of a peptide binding pair in the presence of a test sample, comprising:
(i) culturing at least one yeast cell, wherein the yeast cell comprises;
a) a nucleotide sequence encoding a first heterologous fusion protein comprising the first peptide of a known peptide binding pair that bind through extracellular interaction in their natural environment, or a segment thereof, joined to a transcriptional activation protein DNA binding domain;
b) a nucleotide sequence encoding a second heterologous fusion protein comprising the second peptide, or a segment thereof, joined to a transcriptional activation protein transcriptional activation domain; wherein binding of the first peptide or segment thereof and the second peptide or segment thereof reconstitutes a transcriptional activation protein; and
c) a luciferase gene activated under positive transcriptional control of the reconstituted transcriptional activation protein;
(ii) incubating the test sample with the yeast cell under conditions suitable to detect expression of the luciferase gene; and
(iii) detecting the interaction of the first peptide and the second peptide by determining the level of expression of the luciferase gene.

30. The method of claim 29 wherein the yeast cell further comprises at least one endogenous nucleotide sequence selected from the group consisting of a nucleotide sequence encoding the transcriptional activation protein DNA binding domain, and a nucleotide sequence encoding the transcriptional activation protein transcriptional activation domain wherein at least one of the endogenous nucleotide sequences is inactivated by mutation or deletion.

31. The method of claim 29 wherein the peptide binding pair comprises a ligand and a receptor to which the ligand binds.

32. The method of claim 29 wherein the transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

33. The method of claim 29 wherein at least one of the heterologous fusion proteins is expressed from an autonomously-replicating plasmid.

34. The method of claim 33 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

35. The method of claim 34 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

36. The method of claim 29 wherein the DNA binding domain is a heterologous transcriptional activation protein DNA-binding domain.

37. The method of claim 36 wherein the DNA binding protein is selected from the group consisting of a mammalian steroid receptor and bacterial LexA protein.

38. The method of claim 29, wherein the yeast cell is *Saccharomyces cerevisiae, Schizosaccharomyces pombe,* or *Pichia pastoris.*

39. The method of claim 38, wherein the yeast cell is *Saccharomyces cerevisiae.*

40. The method of claim 29 wherein the luciferase gene is a Renilla luciferase gene.

41. The method of claim 29, wherein the luciferase gene is a Photinus luciferase gene.

42. The method of claim 29, wherein the first and second peptides of the peptide binding pair interact through extracellular interaction in their natural environment.

43. A method for determining whether a test sample interacts with a first or second peptide of a peptide binding pair, comprising:
(i) culturing at least one first yeast cell, wherein the first yeast cell comprises;
a) a nucleotide sequence encoding a first heterologous fusion protein comprising the first peptide or a segment thereof joined to a transcriptional activation protein DNA binding domain;
b) a nucleotide sequence encoding a second heterologous fusion protein comprising the second peptide or a segment thereof joined to a transcriptional activation protein transcriptional activation domain;
wherein the nucleotide sequence encoding the first heterologous fusion protein is present in an effective copy number of at least 5 copies per yeast cell and the nucleotide sequence encoding the second heterologous fusion protein is present at a copy number of 1 or 2 per yeast cell; and
wherein binding of the first peptide or segment thereof and the second peptide or segment thereof reconstitutes a transcriptional activation protein; and
c) a luciferase gene activated under positive transcriptional control of the reconstituted transcriptional activation protein;
(ii) culturing at least one second yeast cell, wherein the second yeast cell comprises;
a) a nucleotide sequence encoding the first heterologous fusion protein comprising the first peptide or a segment thereof joined to a transcriptional activation protein DNA binding domain;
b) a nucleotide sequence encoding the second heterologous fusion protein comprising the second peptide or a segment thereof joined to a transcriptional activation protein transcriptional activation domain;
wherein the nucleotide sequence encoding the second heterologous fusion protein is present in an effective copy number of at least 5 copies per yeast cell and the nucleotide sequence encoding the first heterologous fusion protein is present at a copy number of 1 or 2 per yeast cell; and
wherein binding of the first peptide or segment thereof and the second peptide or segment thereof reconstitutes a transcriptional activation protein; and
c) a luciferase gene activated under positive transcriptional control of the reconstituted transcriptional activation protein;
(iii) incubating a test sample with the first and second yeast cells under conditions suitable to detect luciferase activity;
(iv) detecting the luciferase activity produced by the first and second yeast cells; and
(v) comparing the detected luciferase activity of the first and second yeast cells, wherein lower luciferase activity in one of the yeast cells compared to the other yeast cell indicates that the test sample binds to the heterogeneous fusion protein encoded by the nucleotide sequence present at a copy number of 1 or 2 in that yeast cell exhibiting lower luciferase activity, thereby affecting the binding interaction of the peptide binding pair.

44. The method of claim 43 wherein either or both of the first and second yeast cells further comprises at least one endogenous nucleotide sequence selected from the group consisting of a nucleotide sequence encoding the transcriptional activation protein DNA binding domain and a nucleotide sequence encoding the transcriptional activation protein transcriptional activation domain, wherein at least one of the endogenous nucleotide sequences Is inactivated by mutation or deletion.

45. The method of claim 43 wherein the peptide binding pair comprises a ligand and a receptor for the ligand.

46. The method of claim 43 wherein the transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

47. The method of claim 43 wherein at least one of the heterologous fusion proteins is expressed from an autonomously-replicating plasmid.

48. The method of claim 47 wherein at least one peptide of the peptide binding pair is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

49. The method of claim 48 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M, ciliary neurotrophic factor, erythropoietin, steel factor, placental lactogen, and TGF.

50. The method of claim 43 wherein the DNA binding domain is a heterologous transcriptional activation protein DNA-binding domain.

51. The method of claim 50 wherein the DNA binding protein is selected from the group consisting of a mammalian steroid receptor and bacterial LexA protein.

52. The method of claim 43 wherein the yeast cell is *Saccharomyces cerevisiae, Schizosaccharomyces pombe,* or *Pichia pastoris.*

53. The method of claim 52 wherein the yeast cell is *Saccharomyces cerevisiae.*

54. The method of claim 43 wherein the luciferase gene is a Renilla luciferase gene.

55. The method of claim 43 wherein the luciferase gene is a Photinus luciferase gene.

56. The method of claim 43 wherein the first and second peptides of the peptide binding pair interact through extracellular interaction in their natural environment.

57. A method of simultaneously detecting the interaction of two different peptide binding pairs in the presence of at least one test sample, wherein the first peptide binding pair comprises a first peptide and a second peptide, and wherein the second peptide binding pair comprises a third peptide and a fourth peptide, comprising:
(i) culturing at least one yeast cell, wherein the yeast cell comprises;
a) a nucleotide sequence encoding a first heterologous fusion protein comprising the first peptide or a segment thereof joined to a DNA binding domain of a first transcriptional activation protein;
b) a nucleotide sequence encoding a second heterologous fusion protein comprising the second peptide or segment thereof joined to a transcriptional activation domain of the first transcriptional activation protein;
c) a nucleotide sequence encoding a third heterologous fusion protein comprising the third peptide or segment thereof joined to a DNA binding domain of a second transcriptional activation protein;
d) a nucleotide sequence encoding a fourth heterologous fusion protein comprising the fourth peptide or a segment thereof joined to a transcriptional activation domain of the second transcriptional activation protein;
wherein binding of the first peptide or segment thereof and the second peptide or segment thereof reconstitutes the first transcriptional activation protein, and binding of the third peptide or segment thereof and the fourth peptide or segment thereof reconstitutes the second transcriptional activation protein;

e) a first luciferase gene activated under positive transcriptional control of the first reconstituted transcriptional activation protein;

f) a second luciferase gene activated under positive transcriptional control of the second reconstituted transcriptional activation protein; and (ii) incubating the at least one test sample with the yeast cell under conditions suitable to detect luciferase activity; and (iii) detecting the interaction of the first peptide and the second peptide by determining the level of expression of the first luciferase gene and detecting the interaction of the third peptide and the fourth peptide by determining the level of expression of the second luciferase gene.

58. The method of claim 57 wherein the yeast cell further comprises at least one endogenous nucleotide sequence selected from the group consisting of a nucleotide sequence encoding the transcriptional activation protein DNA binding domain, and a nucleotide sequence encoding the transcriptional activation protein transcriptional activation domain wherein at least one of the endogenous nucleotide sequences is inactivated by mutation or deletion.

59. The method of claim 57 wherein at least one of the peptide binding pairs comprises a ligand and a receptor to which the ligand binds.

60. The method of claim 57 wherein the first or second transcriptional activation protein is Gal4, Gcn4, Hap1, Adr1, Swi5, Ste12, Mcm1, Yap1, Ace1, Ppr1, Arg81, Lac9, Qa1F, VP16, or a mammalian nuclear receptor.

61. The method of claim 57 wherein at least one of the heterologous fusion proteins is expressed from an autonomously-replicating plasmid.

62. The method of claim 61 wherein at least one peptide of the peptide binding pairs is selected from the group consisting of a cytokine, an interleukin, a hematopoietic growth factor, insulin, an insulin-like growth factor, a growth hormone, prolactin, an interferon, a growth factor, a ligand for G-protein coupled receptors, a ligand for guanylyl cyclase receptors, a ligand for tyrosine phosphatase receptors, and a ligand for tyrosine kinase receptors.

63. The method of claim 62 wherein the peptide is a growth factor selected from the group consisting of epidermal growth factor, nerve growth factor, leukemia inhibitory factor, fibroblast growth factor, platelet-derived growth factor, vascular endothelial growth factor, tumor necrosis factor, oncostatin M. ciliary neurotrophic factor, erythropoietin, steel factor, placental lactogen, and TGF.

64. The method of claim 57 wherein the DNA binding domain is a heterologous transcriptional activation protein DNA-binding domain.

65. The method of claim 64 wherein the DNA binding protein is selected from the group consisting of a mammalian steroid receptor and bacterial LexA protein.

66. The method of claim 57, wherein the yeast cell is *Saccharomyces cerevisiae, Schizosaccharomyces pombe,* or *Pichia pastoris.*

67. The method of claim 66, wherein the yeast cell is *Saccharomyces cerevisiae.*

68. The method of claim 57 wherein the first and second peptides of the peptide binding pair interact through extracellular interaction in their natural environment.

* * * * *

UNITED STATES PATENT AND TRADEMARK OFFICE
CERTIFICATE OF CORRECTION

PATENT NO. : 6,770,446 B1
DATED : August 3, 2004
INVENTOR(S) : Kathleen Young et al.

It is certified that error appears in the above-identified patent and that said Letters Patent is hereby corrected as shown below:

<u>Column 35,</u>
Line 8, "Qal F," should read -- QalF, --.
Line 30, "DNA binding" should read -- DNA-binding --.

<u>Column 37,</u>
Line 60, "Is" should read -- is --.

<u>Column 40,</u>
Line 15, "M." should read -- M, --.

Signed and Sealed this

Twenty-third Day of November, 2004

JON W. DUDAS
*Director of the United States Patent and Trademark Office*

SEQUENCE LISTING

<160> NUMBER OF SEQ ID NOS: 22

<210> SEQ ID NO 1
<211> LENGTH: 30
<212> TYPE: DNA
<213> ORGANISM: Sus sp.

<400> SEQUENCE: 1
catgccatgg aggccttccc agccatgccc                30

<210> SEQ ID NO 2
<211> LENGTH: 27
<212> TYPE: DNA
<213> ORGANISM: Sus sp.

<400> SEQUENCE: 2
cgggatccgc aactagaagg cacagct                27

<210> SEQ ID NO 3
<211> LENGTH: 33
<212> TYPE: DNA
<213> ORGANISM: Rattus norvegicus

<400> SEQUENCE: 3
catgccatgg agatgtttcc tggaagtggg gct                33

<210> SEQ ID NO 4
<211> LENGTH: 39
<212> TYPE: DNA
<213> ORGANISM: Rattus norvegicus

<400> SEQUENCE: 4
catgccatgg cctaccggaa atcttcttca catgctgcc                39

<210> SEQ ID NO 5
<211> LENGTH: 38
<212> TYPE: DNA
<213> ORGANISM: Sus sp.

```
<400> SEQUENCE: 5
ccgaattcaa aatggccttc ccagccatgc ccttgtcc                               38

<210> SEQ ID NO 6
<211> LENGTH: 26
<212> TYPE: DNA
<213> ORGANISM: Sus sp.

<400> SEQUENCE: 6
ccaagcttca actagaaggc acagct                                            26

<210> SEQ ID NO 7
<211> LENGTH: 31
<212> TYPE: DNA
<213> ORGANISM: Sus sp.

<400> SEQUENCE: 7
cggaattctg cccatctgcc ccagcgggcc t                                      31

<210> SEQ ID NO 8
<211> LENGTH: 30
<212> TYPE: DNA
<213> ORGANISM: Sus sp.

<400> SEQUENCE: 8
gaattcacgt gggcttagca gttgctgtcg                                        30

<210> SEQ ID NO 9
<211> LENGTH: 31
<212> TYPE: DNA
<213> ORGANISM: Sus sp.

<400> SEQUENCE: 9
tcccccgggg atgtcatctg cacttgctta c                                      31

<210> SEQ ID NO 10
<211> LENGTH: 31
<212> TYPE: DNA
<213> ORGANISM: Sus sp.

<400> SEQUENCE: 10
tccgtcgacg gtctttcaag gtgaagtcat t                                      31

<210> SEQ ID NO 11
<211> LENGTH: 33
<212> TYPE: DNA
<213> ORGANISM: Sus sp.

<400> SEQUENCE: 11
gaattcaaaa tgctgcccat ctgccccagc ggg                                    33

<210> SEQ ID NO 12
<211> LENGTH: 27
<212> TYPE: DNA
<213> ORGANISM: Saccharomyces cerevisiae

<400> SEQUENCE: 12
ggatccaatc aagaatgcct tccagat                                           27

<210> SEQ ID NO 13
<211> LENGTH: 24
<212> TYPE: DNA
```

-continued

<213> ORGANISM: Saccharomyces cerevisiae

<400> SEQUENCE: 13
gcatgcgtca tagaaataat acag                    24

<210> SEQ ID NO 14
<211> LENGTH: 34
<212> TYPE: DNA
<213> ORGANISM: Homo sapiens

<400> SEQUENCE: 14
cggaattcga agtatggcac ccatggcaga agga          34

<210> SEQ ID NO 15
<211> LENGTH: 28
<212> TYPE: DNA
<213> ORGANISM: Homo sapiens

<400> SEQUENCE: 15
cggaattcgg atcctcattc attcatca                 28

<210> SEQ ID NO 16
<211> LENGTH: 21
<212> TYPE: DNA
<213> ORGANISM: Photinus pyralis

<400> SEQUENCE: 16
tcaaattaac aaccatagga t                        21

<210> SEQ ID NO 17
<211> LENGTH: 31
<212> TYPE: DNA
<213> ORGANISM: Homo sapiens

<400> SEQUENCE: 17
accatgggat gtcggcaaag ctcagaggaa a             31

<210> SEQ ID NO 18
<211> LENGTH: 18
<212> TYPE: DNA
<213> ORGANISM: Homo sapiens

<400> SEQUENCE: 18 caagggtgg gggacatt                             18

<210> SEQ ID NO 19
<211> LENGTH: 18
<212> TYPE: DNA
<213> ORGANISM: Homo sapiens

<400> SEQUENCE: 19
cccggccggc aggtggac                            18

<210> SEQ ID NO 20
<211> LENGTH: 23
<212> TYPE: DNA
<213> ORGANISM: Homo sapiens

<400> SEQUENCE: 20
ctcatgcaaa ataaaagtgg ttc                      23

<210> SEQ ID NO 21
<211> LENGTH: 21

-continued

```
<212> TYPE: DNA
<213> ORGANISM: Homo sapiens

<400> SEQUENCE: 21
gtgggggggc tgaggtcaga g                                        21

<210> SEQ ID NO 22
<211> LENGTH: 21
<212> TYPE: DNA
<213> ORGANISM: Homo sapiens

<400> SEQUENCE: 22
ctctgacctc agccccccca c                                        21
```